(12) United States Patent
Mueller et al.

(10) Patent No.: US 12,232,986 B2
(45) Date of Patent: Feb. 25, 2025

(54) LINER SYSTEM AND METHOD FOR APPLYING A LINER SYSTEM

(71) Applicant: Ottobock SE & Co. KGaA, Duderstadt (DE)

(72) Inventors: Christian Mueller, Kalefeld (DE); Thilo-Mathias Bielefeld, Siedenlangenbeck (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 406 days.

(21) Appl. No.: 16/603,942

(22) PCT Filed: Apr. 25, 2018

(86) PCT No.: PCT/EP2018/060624
§ 371 (c)(1),
(2) Date: Oct. 9, 2019

(87) PCT Pub. No.: WO2018/197574
PCT Pub. Date: Nov. 1, 2018

(65) Prior Publication Data
US 2020/0060846 A1    Feb. 27, 2020

(30) Foreign Application Priority Data
Apr. 26, 2017   (DE) .......................... 102017108913.6

(51) Int. Cl.
*A61F 2/78* (2006.01)
*A61F 2/80* (2006.01)

(52) U.S. Cl.
CPC .............. *A61F 2/7812* (2013.01); *A61F 2/80* (2013.01); *A61F 2002/7837* (2013.01); *A61F 2002/785* (2013.01); *A61F 2002/802* (2013.01)

(58) Field of Classification Search
CPC .. A61F 2/7812; A61F 2/80; A61F 2002/7837; A61F 2002/785;
(Continued)

(56) References Cited

U.S. PATENT DOCUMENTS 5,376,127 A * 12/1994 Swanson .................. A61F 2/78
623/901
6,508,842 B1 * 1/2003 Caspers ................ A61F 2/5046
623/32

(Continued)

FOREIGN PATENT DOCUMENTS

CN           101854888 A      10/2010
CN           101969889 A       2/2011
(Continued)

OTHER PUBLICATIONS

O&P Edge Magazine. New Vacuum Liner Compliments Vac-Pin System. Oct. 2010. (Year: 2010).*

(Continued)

*Primary Examiner* — Christie Bahena
(74) *Attorney, Agent, or Firm* — HOLLAND & HART LLP

(57) ABSTRACT

A liner system for applying to a limb or a limb stump, with an inner liner comprising an inner side facing the limb or limb stump and an outer side facing away from the limb or limb stump, and an outer liner that comprises an inner side facing the inner liner and an outer side facing away from the inner liner. The outer liner is designed to be applied over the inner liner, with a sealing element which is designed to be separate from the inner liner and the outer liner, for arranging between the outer side of the inner liner and the inner side of the outer liner.

22 Claims, 21 Drawing Sheets

(58) Field of Classification Search
CPC ........ A61F 2002/802; A61F 2002/6863; A61F 2002/742; A61F 2002/748; A61F 2002/7875; A61F 2002/805; A61F 2002/807; A61F 2/68; A61F 2/78
See application file for complete search history.

(56) References Cited

U.S. PATENT DOCUMENTS

| | | | |
|---|---|---|---|
| 8,052,760 B2* | 11/2011 | Egilsson | A61F 2/7812 623/36 |
| 8,097,043 B2 | 1/2012 | Egilsson | |
| 9,192,488 B2 | 11/2015 | Bielefeld | |
| 2004/0236434 A1 | 11/2004 | Carstens | |
| 2004/0243252 A1* | 12/2004 | Carstens | A61F 2/80 623/36 |
| 2005/0240283 A1* | 10/2005 | Kania | A61F 2/7812 623/36 |
| 2008/0188949 A1* | 8/2008 | MacKenzie | A61F 2/7812 623/36 |
| 2013/0123940 A1* | 5/2013 | Hurley | A61F 2/54 623/33 |
| 2015/0142133 A1* | 5/2015 | Egilsson | A61F 2/80 623/36 |
| 2017/0105853 A1 | 4/2017 | Johnsson | |

FOREIGN PATENT DOCUMENTS

| | | |
|---|---|---|
| CN | 103930073 A | 3/2016 |
| CN | 105377197 A | 9/2017 |
| CN | 106535830 A | 11/2018 |
| DE | 10142491 A1 | 4/2003 |
| DE | 69826917 T2 | 10/2005 |
| DE | 102014006689 A1 | 11/2015 |
| EP | 870485 B1 | 10/2004 |
| WO | 2004060136 A2 | 7/2004 |
| WO | 2013028647 A1 | 8/2012 |
| WO | 2015073793 A1 | 5/2015 |

OTHER PUBLICATIONS

ESP. Self Adhesive Silicone Strips and Sheets. ESP Website via the wayback machine. Mar. 2016. (Year: 2016).*
"International Search Report and Written Opinion of the International Searching Authority," issued in connection with Int'l Appl. No. PCT/EP2018/060624, dated Jul. 2, 2018 (15 pages).

* cited by examiner

LINER SYSTEM AND METHOD FOR APPLYING A LINER SYSTEM

CROSS REFERENCE TO RELATED APPLICATIONS

This application is a U.S. National Entry and claims priority to PCT International Patent Application No. PCT/EP2018/060624, filed Apr. 25, 2018, and entitled LINER SYSTEM AND METHOD FOR APPLYING A LINER SYSTEM, which claims priority to European Patent Application No. 102017108913.6 filed Apr. 26, 2017, the entire disclosures of which are incorporated herein by this reference.

TECHNICAL FIELD

The invention relates to a liner system for applying to a limb or a limb stump, with an inner liner comprising an inner side facing the limb or limb stump and an outer side facing away from the limb or limb stump, and an outer liner that comprises an inner side facing the inner liner and an outer side facing away from the inner liner and that is designed to be applied over the inner liner. The invention also relates to a method for applying such a liner system. This type of liner system is especially intended for use as a prosthetic liner system for applying a prosthetic component, in particular a prosthetic socket, to a limb stump. In principle, it is also possible for orthoses to be fixed to the limb via a liner system. Here, too, there is a need for an increased degree of customisability and at the same time, simple production.

BACKGROUND

Prostheses are intended to replace the function and, where applicable, the form of a limb that does not or no longer exists. To this end, it is necessary for the prosthesis to be attached to the existing limb or to the body of the user of the prosthesis. Various solution systems are available for this purpose, by means of which prosthetic components, particularly a prosthetic socket, can be attached to a limb or a limb stump. Alongside a fixing via belts or straps, nowadays it is increasingly popular to use a liner system which comprises a liner that is pulled over a limb or a limb stump in order to create an interface between the limb stump and the prosthetic socket on which further prosthetic components are arranged. The liner forms both a protective layer for the surface of the skin and a padding for evenly distributing pressure loads. The prosthetic liner also protects the skin from irritations. Furthermore, mechanical locking devices, such as a lock pin or a tension belt, can be fixed to the prosthetic liner, by means of which the prosthetic liner can be securely connected to the prosthetic components that are to be attached to it.

Alongside a locking via a so-called pinlock system or a belt, it is possible to connect the prosthetic socket to the liner via a vacuum system. To this end, the prosthetic liner is pulled over the limb and a sealed volume between the outer side of the prosthetic liner and the inner side of the prosthetic socket formed, from which air is then extracted. A vacuum in the space between the outer side of the prosthetic liner and the inner side of the prosthetic socket holds the prosthetic socket securely in position on the prosthetic liner. To release the prosthetic liner, air is introduced into the gap. To seal the upper edge of the socket, the upper edge of the prosthetic liner, which protrudes above the upper edge of the prosthetic socket, can be folded over. A double-walled liner with a surrounding thickening on the folded-over side of an outer liner is described in US 9 192 488 B2. Alternatively, a sealing lip can be arranged on the outer side of the prosthetic liner in order to guarantee the formation of the closed space between the outer side of the prosthetic liner and the inner side of the prosthetic socket. Such liner systems are described in WO 2004-0601136 A2, for example.

WO 2013/028647 A1 relates to a prosthetic liner for arranging between a stump and a prosthetic socket with an elongated, predominantly conical base body made of an elastic material that can be at least radially stretched. The liner base body comprises proximal and distal end regions. A sealing component is connected to the liner base body and features at least one outer structure along the outer surface of the sealing components for engaging with a prosthetic socket and at least one inner structure for moveably coming into contact with the liner base body.

DE 101 42 491 B4 relates to a sealing arrangement for sealing an amputation stump in a cup-shaped, air-tight prosthetic socket, with a support that can be extended over the amputation stump, said support enclosing the amputation stump on all sides in the circumferential direction. The support features at least one sealing lip, which comprises a root and a supple sealing edge that is positioned away from the root, wherein said sealing edge should lie flat against the inner side of the prosthetic socket such that it forms a seal, wherein the sealing edge lies in a proximal position relative to the amputation stump and in a distal position relative to the root when in use. The sealing lip at least partially surrounds the amputation stump in the circumferential direction and is fixed to the support by way of its root. The back of the sealing lip can be aerated to the surroundings.

DE 10 2014 006 689 A1 relates to a sealing ring for fixing to a proximal end of a stump accommodation, said sealing ring featuring a sleeve-shaped base body which comprises fastening elements for attaching the base body to the stump accommodation. A sealing lip is arranged on the base body, said sealing lip facing inwards.

US 8 8,097,043 B2 relates a prosthetic liner with an elongated, primarily conical base body made of a material that can be at least radially stretched and that forms an open proximal and a closed distal end. The outer-most layer of the base body is formed by a textile seal. At least one flexible sealing element made of an elastomer material extends along the outer-most layer. At least one sealing element extends outwards from the distal area to the proximal area, such that the thickness of the at least one sealing element in the proximal area is greater than the thickness in the distal area. The proximal area has a cross-section that extends essentially perpendicular to the longitudinal direction of the liner base body. The at least one sealing element extends in a ring shape around the base body at its distal end.

A liner with a moulded outer sealing lip is comparatively difficult to produce. A double-walled liner that is to be folded over the edge of the prosthetic socket requires additional material and results in an increase in the circumference in the proximal region of the prosthetic socket. It is also not possible to customize the prosthetic liner.

SUMMARY

The task of the present invention is to provide a liner system and a method for applying a liner which allow for simple customizing and a simple and cost-effective production.

According to the invention, this task is solved by a liner system and a prosthesis system as disclosed herein. Advantageous configurations and embodiments of the invention are found in the description and the figures.

The liner system for applying to a limb or a limb stump, with an inner liner comprising an inner side facing the limb or limb stump and an outer side facing away from the limb or limb stump, and an outer liner that comprises an inner side facing the inner liner and an outer side facing away from the inner liner and that is designed to be applied over the inner liner provides that a sealing element, which is designed to be separate from the inner liner and the outer liner, be configured for arranging between the outer side of the inner liner and the inner side of the outer liner. When the liner system is mounted, the sealing element is held between the inner liner and the outer liner. The inner liner lies closely on the limb or the limb stump; the sealing element lies closely on the inner liner and is covered by the outer liner. It is not necessary for the outer liner to cover the entire outer side of the inner liner. The sealing element arranged between the inner liner and the outer liner serves to increase the material thickness in the area around the sealing element, such that an increased surface pressure can build on the outer side of the outer liner. The initially preferred smooth-walled outer side of the outer liner is contoured by the sealing element between the inner liner and the outer liner. Due to the separate configuration of the sealing element from the inner liner and the outer liner, it is possible to provide a liner system, especially a liner for the use of a prosthesis on a lower limb, whose sealing element can be used and positioned in a variety of ways. It is therefore possible, on the one hand, to safely create and maintain a vacuum in a prosthetic socket by providing an internal seal with an increased surface pressure in an area between a distal end and a proximal edge of a prosthetic socket, and on the other hand to design the height of the seal on the limb or the limb stump in such a way that it can be freely selected. Due to the fact that the position of the sealing element on the inner liner can generally be freely selected, a simple adjustment to the respective conditions of the limb or the stump, or to the interaction between the limb, the limb stump and the surrounding prosthetic or orthotic components can be achieved. According to the invention, the liner system provides a double-walled design, which enables an improved protective effect for the limb or the limb stump. The sealing element is arranged, in particular applied and placed in the desired position, between the layers of the double-walled liner, wherein the individual arrangement of the sealing element on the outer side of the inner liner renders a multitude of liner models with moulded sealing lips no longer necessary. The outer liner can be designed such that it can be shortened so as to allow for an adjustment to the respective physical dimensions of the user, such that the liner system has no effect on the flexion movement. In the case of transtibial amputations, the liner can be shortened below the hollow of the knee; an influence on the knee flexion is thus prevented.

A further embodiment of the invention proposes that the sealing element be designed to be ring-shaped, wherein the ring-shaped sealing element may feature a multitude of different inner and outer diameters, said sealing element having a closed circumference, in order to carry out an adjustment to different operating conditions in a simple and cost-effective manner. The provision of a multitude of sealing elements—in the form of sealing rings—that are simple to produce and inexpensive allows for a cost-effective adjustment to the respective patient, carried out by a user or an othopedic technician, with predominantly standardised inner liners and outer liners by selecting and using the appropriate sealing ring or the appropriate sealing element.

As an alternative to a ring-shaped sealing element with a closed circumference, the sealing element may also be designed to be belt-like, wherein the sealing element is then placed around the circumference, preferably fully around the circumference, of the inner liner, in order to achieve a preferably circumferential seal and an enlargement of the cross-section in the area around the sealing element. Following the application and arrangement of the outer layer over the sealing element, a partial increase in the outer diameter across the longitudinal direction of the liner system is achieved in order to enable an improved sealing effect in this region by way of an increased surface pressure of the outer liner on the inner circumference of the socket or the applied orthopedic device. With a belt-like configuration of the sealing element, it is possible that the design encompasses free ends which need not be joined to a closed cross-section; one variation proposes that free ends of a belt-like sealing element overlap with one another or are arranged on the outer side of the inner liner in the manner of a spiral, resulting in the creation of a closed circumference when considering the sealing element in the longitudinal direction of the inner liner. The free ends can be laid over one another and intersect at an acute angle; alternatively, the free ends are laid next to one another in the axial direction of the inner liner. The free ends may be laid on top of one another or positioned at a distance from one another in the axial or longitudinal direction on the inner liner.

Fixing elements may be configured on or fixed to the sealing element in order to connect free ends of a belt-like sealing element to one another. The connection may be positive-locking, for example by way of the slotting in, snapping or catching of undercuts configured on the sealing element. Fixing elements or at least one fixing element may also be designed to be separate and arranged separately on the sealing element, for instance in the form of an adhesive layer or a double-sided adhesive tape. The sealing element can be fixed or positioned at snap-in points or snap surfaces on the outer side of the inner liner. The snap-in points or snap surfaces may prevent or at least render more difficult a displacement of the sealing element during use.

The cross-section of the sealing element may be designed to be solid in order to prevent a compression and thereby a reduction in the cross-section of the sealing element upon application of the socket over the outer liner. This results in a high surface pressure; however, it may also lead to an increase in the pressure on the inner liner and thus on the limb or the limb stump. The cross-section may also be designed as a hollow cross-section in order to achieve a compression and reduction in the cross-section of the sealing element. A close-walled hollow cross-section enables compression by way of deformation. A restoring force is exerted by the volume enclosed in the sealing element or by way of the elastic design of the sealing element, thereby enabling a restriction on the compressive force and a compensation for fluctuations in volume. The cross-section of the sealing element may also be designed as an open hollow profile, for instance L-shaped or triangular with a roof-like area that protrudes outwards, which enables a simplified deformation of the cross-section up until the point at which the roof section can be laid on a base section. Once the base is reached and the roof section lies upon it, there is an increase in the deformation resistance, such that a greater resistance occurs with an increase in compression from the outside. It is possible to combine all cross-section forms, i.e. solid, a closed hollow cross-section, an open cross-section or an open hollow cross-section, or where appropriate only two of the cross-section forms, in order to provide the respective properties of the selected cross-section for the sealing element on an area-by-area basis.

The sealing element may be made of a foam or feature or be filled with a foam or textile. In particular, if the sealing element is designed as a hollow cross-section, be it a closed or an open hollow cross-section, the hollow cross-section can be fully or partially foamed or feature or be filled with a volume element, such as a textile or a foam material. Specifically, the textile may be designed as a textile spacer fabric that causes an increase in volume without considerably altering the compressibility or deformability of the sealing element. Depending on the robustness of the textile or the spacer fabric, the firmness of the sealing element can be varied. The same applies to the complete or partial filling of the hollow cross-section with a foam. In an embodiment of the invention, rather than filling it with a foam, the sealing element itself is made of a foamed material, a foam, in order to create a volume between the inner liner and the outer liner, so as to create a sealing effect.

In another embodiment, the elastic volume element may be provided with a coating that increases the friction coefficient of the sealing element and thus ensures a fixed position of the sealing element on the inner liner. Preferably, the elastic sealing element has a low degree of hardness or can be easily compressed so as not to partially increase the pressure on the patient's stump too severely. The sealing ring may also be made of a hollow body that can be or is filled with a fluid. The fluid renders it possible to additionally adjust the volume or the properties of the sealing ring to correspond to the needs of the user. To this end, the hollow body can be filled with a fluid or a compressible fluid, such as air.

The form of the cross-section of the sealing element may be also be designed to be round, triangular, quadrangular or polygonal, where appropriate with a flat contact surface, such that different contact properties and thus sealing properties for the liner system can be adjusted via different forms of the cross-section of the sealing element. The form of the cross-section can be changed via the length or the circumference of the sealing element; in addition to circular cross-sections, the cross-section may also be designed to be rounded, oval or feature a flat contact surface and an adjoining round.

The sealing element preferably consists of an elastic material, especially an elastomer such as silicon, in order to ensure a secure attachment and positioning of the sealing element on the inner liner before the sealing element is covered on the outside by the outer liner, especially if said sealing element is designed to be ring-shaped; this is achieved by expanding the sealing element during placement and application on the outer side of the inner liner. Given that the sealing element or the sealing ring is made of a material that can be slightly stretched in the radial direction, the liner can be rolled up or down to make it easier to put on and remove. To this end, the sealing element or the sealing ring preferably consists of a foam, in addition to an elastomer. Other volume elements, such as a soft elastic spiral spring that can be expanded radially, are suitable sealing elements.

To avoid a displacement of the sealing element following its application on the inner liner, an embodiment of the invention proposes that the sealing element sticks to the outer side of the inner liner and/or to the inner side of the outer liner. Here, the sealing element is made of an appropriate material or at least partially features a coating that allows it to be stuck on the inner liner and/or outer liner.

An embodiment of the invention proposes that the inner liner and/or outer liner comprise—on either an individual or joint basis—a closed distal end region, so that they can be placed over the distal end of the stump and form a distal termination, particularly if they are designed as prosthetic liners. If the inner liner and outer liner are designed to be close-walled, the respective closed distal end region results in a sleeve-shaped liner that is open on one side with an insertion opening, wherein said liner can be pulled over the respective stump. This is generally achieved by turning the inner side of inner liner or the outer liner outwards, i.e. inside-out. The tip of the stump is placed at the front end region of the upside-down liner; the rest of the liner is then rolled up or pulled onto the stump, such that the original inner side once again lies on the side facing the stump. If both the inner liner and the outer liner have a closed distal end region, a double-walled liner is also provided in this region, which is especially subjected to compressive forces; this double-walled liner can absorb and distribute compressive forces. The distal end region or distal end regions may comprise an additional padding or a greater material strength compared to the rest of the liner in order to ensure a more effective padding effect and a greater degree of dimensional stability. It is generally also possible for only the inner liner or the outer liner to designed to be close-walled, so as to achieve a sealing of the hollow space between the prosthetic socket or the orthopedic device that is placed around the liner.

A variation of the invention sees the inner liner and outer liner being attached to one another to facilitate application. For their application, the inner liner and outer liner are then turned outwards together, as described above, so that they can be applied to the stump at the same time.

An advantageous embodiment of the invention proposes that the inner liner and the outer liner be connected to one another in their distal end regions in either a positive-locking or bonded manner, and that they form a connection zone in the distal end region, wherein it is not readily possible to insert a sealing element between the inner liner and the outer liner in said connection zone. In a bonded configuration that features an elastomer material, the inner liner and outer liner are cured, wherein the bonded connection can be also be achieved by curing two already partially cured components, i.e. partially cured inner and outer liners. It is also possible for the inner liner and the outer liner to be cast in a joint manufacturing process. The gap between the inner liner and the outer liner, into which the sealing element is then introduced, is formed by way of a separation element, so that the connection zone is a one-piece distal end region to which two, generally thin-walled, inner liner sections and outer liner sections are connected in the proximal direction. Sections of the inner liner may be glued or welded to the outer liner. The inner liner and the outer liner may also be reversibly attached to one another, for example by way of adhesive properties of the elastomer or positive-locking elements, velcro fasteners or other catch or locking elements, which can be used to attach the outer liner to the inner liner such that it can be detached. The inner liner may also be permanently fixed to the outer liner via positive-locking elements on the inner liner. In the proximal region of the outer liner, the inner liner and outer liner are not connected to one another, so as to ensure a sufficiently large area for the arrangement of a sealing element.

To increase the level of comfort when being worn, the inner liner and/or the outer liner comprise a closed cross-section in order to prevent pressure sores from forming at overlaps. It is generally also possible to provide an open cross-section with end regions that overlap with one another and that have reduced material strength, so that no thickening occurs in the overlapping areas. A close-walled, sleeve-like structure of both the outer liner and the inner liner renders both application and wear easier, as well as ensuring that they are and remain largely gas-tight. The inner liner may also feature an open cross-section; here, the edges that lie opposite one another then preferably abut one another following application. The sealing element then fixes the position of edges relative to one another. Once the outer liner has been pulled over, the arrangement of the components relative to one another is further secured.

The outer liner or the outer liner and inner liner are preferably made of or with an elastomer, for example silicon or another elastomer. To ensure safe functioning, it is especially important that the outer liner be made of an elastomer or that it comprises a coating on its outer side that is elastic and gas-proof in order to guarantee a secure seal between the outer side of the outer liner and the inner side of a socket or an accommodation sleeve. An elastic or elastomer design of the outer liner or the outer liner and the inner liner renders it possible to compensate for any fluctuations in volume of the stump or the limb, but also to cater for different limb or stump dimensions with one liner model or liner size. This renders it possible to cater for a large range of limbs or stumps with a manageable number of liners.

The inner liner and outer liner are preferably made of the same material; in principle, it is also possible for the inner liner and outer liner to be made of different materials, for example to meet different demands by using different materials. For instance, an increased degree of breathability or permeability for air or moisture may be beneficial for the inner liner in order to increase the level of comfort, whereas for the outer line, it is essential to ensure that it is gas-proof and dimensionally stable, so as to guarantee a safe application and sealing relative to the socket or the outer casing or sleeve. The inner liner may be made of a breathable material that features, at least in some areas, an adhesive coating on its inner side in order to guarantee a secure attachment to the surface of the skin. A variation of the invention proposes that the inner liner be made of a textile that is made especially of a breathable textile, so that moisture can be diverted away from the surface of the skin, thereby increasing the level of comfort felt when it is worn. With regards to the outer liner, its secure arrangement on the inner liner and its seal against the outer lying socket is essential, so that a coupling to the outer side of the inner socket via e.g. catch elements and a gas-proof coating ensures sufficient functionality when the outer liner is designed to be predominantly elastic using TPE, silicon, polyurethane or other suitable elastomers. A reinforcement layer may be incorporated in the inner liner and/or outer liner which is embedded in a carrier matrix, for example made of an elastomer, or applied and connected to said carrier matrix.

If the outer liner and inner liner are connected in the vicinity of a connection zone, it is beneficial if the connection zone does not extend beyond up to the first distal third of the outer liner or the inner liner in the proximal direction, so as to ensure a sufficient degree of versatility regarding the positioning of the sealing element between the inner liner and the outer liner. By producing a small number of liner lengths with a relatively long separation area between the inner liner and outer liner in the proximal section, it is thus possible to position the sealing element at the desired points and in the desired position in a arbitrary or virtually arbitrary manner. This renders the liner highly customizable and means that the liner system can be universally applied; only the length need be adjusted by way of shortening it.

Markers may be arranged or configured on the inner liner for the purpose of arranging the sealing element. Specifically, the markers are visual markers; however, it is generally also possible for grooves or notches or elevations to be arranged on the outer side of the inner liner so as to facilitate a positioning for the orthopedic technician or the respective user. The markers can also be used to make positions or dimensions, especially the positioning of a distal end of the liner system, easily recognizable in order to ensure a reproducible correct arrangement of the sealing element.

Along with the outer liner, the inner side of the inner liner preferably forms a smooth-walled inner surface, so as to prevent the formation of pressure sores or pinching or wrinkling with the skin of the limb or the limb stump. If the inner liner is designed to be distally closed with just one insertion opening at the proximal end, the smooth-walled surface design of the inner liner is already guaranteed. If the system consists of an inner liner and an outer liner, the outer liner may form a closed distal cap that leads into a step, wherein said step generally corresponds to the material thickness of a solely sleeve-like inner liner, such that the inner liner and outer liner are positioned and joined in such a way upon application that the inner liner abuts the step and forms a smooth-walled inner surface, in order to increase the level of comfort when worn. The inner liner may then be designed as a sleeve without a distal end cap.

The method according to the invention for applying a liner system as described above, in particular a prosthetic liner system, first of all proposes the step of applying an inner liner around a limb or limb stump. A sealing element is subsequently applied on an outer side of the inner liner and the sealing element is positioned on the outer side of the inner liner. Following the application of the sealing element, an outer liner is arranged on the outer side of the inner liner and the sealing element is covered. The subsequent arrangement of a separate sealing element on the outer side of the previously applied inner liner facilitates a simple adjustment of the position of the sealing element to fit the respective user and renders it possible to individually set an optimal position. Neither a multitude of pre-prepared prosthetic liners nor the individual production of a prosthetic liner with an outer sealing lip is required to achieve an optimal positioning of the sealing element on the patient. The production of the inner liner, the sealing element and outer liner is simple; there is no need for complicated geometries for a form with a moulded sealing element during the production of a liner. The production of a generally sleeve-shaped, smooth-walled and, where appropriate, distally closed liner is simpler, more cost-effective and less prone to error than the production of a liner with a moulded sealing lip. The user is able to customize both the form and positioning of the sealing element, and an orthopedic technician need not acquire any new techniques. A range of different sealing elements allows for fluctuations in volume of a limb to be easily compensated. If the volume of a limb or limb stump increases, thinner or softer sealing elements can be inserted in order to maintain an even contact pressure. In the event of a decrease in volume, correspondingly stiffer or thicker sealing elements can be inserted between the outer side of the outer liner and the inner side of a socket or a sleeve in order to maintain the required contact pressure, so that adjustments can be undertaken without considerable cost.

An embodiment of the invention proposes that, upon or following the application of the inner liner, the outer liner at least partially covers the outer side of the inner liner, i.e. it is at least partially arranged over the outer side of the inner liner, for instance in order to be able to apply the outer liner to the limb or the stump at the same time as the inner liner. A proximal end of the outer liner is subsequently pulled down in the distal direction, such that the inner side of the outer liner unrolls outwards, thereby partially exposing the outer side of the inner liner prior to the application of the sealing element. The sealing element is then placed on the outer side of the inner liner and the outer liner is rolled or pulled back over the inner liner and the sealing element now arranged on it, such that the outer liner covers the sealing element, thereby fixing it to the inner liner. The dimensions of the outer liner are designed in such a way that, due to its elastic material properties, it lies flat on the outer side of the inner liner, where appropriate slightly compressed, such that the sealing element is pressed onto the outer side of the inner liner. The outer liner, which extends over the inner liner and the sealing element, ensures that the sealing element is not displaced or unrolled by the inner liner by way of shear force, even when the liner system is inserted into a socket or a sleeve.

An embodiment of the invention proposes that the sealing element be applied transversely to the longitudinal direction of the inner liner in order to achieve an optimal positioning of the sealing element and thereby an optimal course of the sealing surface between the outer side of the outer liner and the inner side of the socket or sleeve. Alternatively, the sealing element may be applied to the outer side of the inner liner relative to the longitudinal direction of the inner liner, which generally enables a minimization of the circumference of the sealing element, such that the length or surface on which the sealing element is to act can be minimized.

An embodiment of the invention proposes that the sealing element be fixed to the inner liner following or upon the application to the outer side of the inner liner. As a result, upon the first application of the inner liner around or on a limb or limb stump, the sealing element is arranged and fixed on the outer side of the outer liner, for example it is stuck to it or held by way of inherent tension, for instance if a belt-shaped arrangement of the sealing element can be achieved as a result of adhesive properties of a belt-shaped sealing element, which is arranged with ends or areas that over-lap with one another. The sealing element is preferably fixed to the outer side of the inner liner such that it can be detached in order to allow for the replacement of the sealing elements, if necessary, for example in order to balance out any flatnesses or to be able to adjust sealing elements to meet altered needs or a modified prosthetic socket. If the sealing element is permanently fixed to the inner liner or fixed to the liner such that it can be detached, the positioning of the sealing element on the liner is no longer necessary when re-applying the outer liner; this saves the patient or user of the liner system a step in the operational process.

Across the area which features a double-layered arrangement between the outer liner and the inner liner, the material thickness of the inner liner and/or outer liner is essentially the same or at least continuous, wherein an essentially even reduction in the thickness of the walls may occur from the distal to the proximal. Specifically, no projections or sealing elements are arranged or configured on the outer side of the outer liner.

BRIEF DESCRIPTION OF THE DRAWINGS

In the following, examples of embodiments of the invention will be explained in more detail by way of the attached figures. They show.

DETAILED DESCRIPTION

Figure 1:
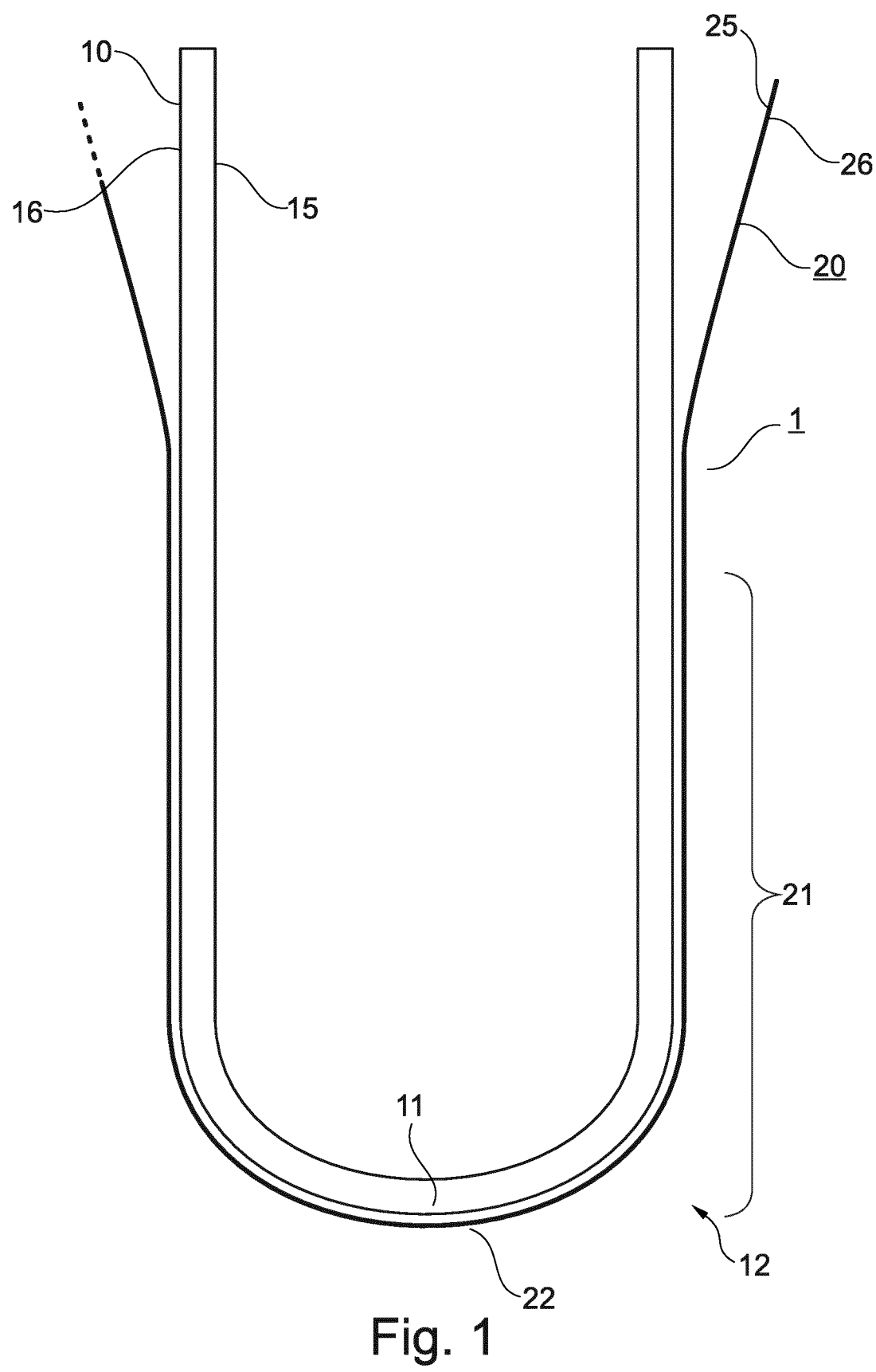
FIG. 1—a liner system with an inner liner and an outer liner in a schematic cross-sectional view.

In a schematic cross-sectional view, FIG. 1 depicts a part of a liner system 1 with an inner liner 10 and an outer liner 20. The inner liner 10 comprises a smooth-walled inner side 15 and an outer side 16, also smooth-walled. The inner liner 10 is designed to be sleeve-shaped and has a distal end region 11 that is designed to be closed, such that a liner body with a closed end cap 12 forms, said liner body being tube-like or sleeve-like, straight-walled or expanding conically towards an insertion opening. An outer liner 20 is arranged on the outer side 16 of the inner liner 10, wherein the inner side 25 of said outer liner lies opposite the outer side 16 of the inner liner. The outer side 26 of the outer liner 20 is designed to be smooth. The form and contour of the inner side 25 of the outer liner 20 generally corresponds to the form and contour of the outer side 16 of the inner liner; where appropriate, the inner contour of the outer liner 20 may feature a smaller diameter or circumference than the outer circumference of the inner liner 10, in order to guarantee sufficient compression of the outer liner 20 against the inner liner 10 when they are arranged on top of one another. For the sake of clarity, the outer liner 20 is shown as expanding conically in the proximal end region, i.e. in the vicinity of the entry opening. The outer liner 20 may comprise a tubular cross-section with a constant diameter or a slightly enlarging conical design. The conical design of the inner liner 10 and the outer liner 20 results in a better application on a stump or limb, which also generally increases conically in the proximal direction, such as a lower leg stump, an upper leg stump or an upper arm stump.

In the example of an embodiment depicted, the inner liner 10 is configured to have a greater wall thickness than the outer liner 20; generally speaking, it is also possible for both the inner liner 10 and the outer liner 20 to have the same material thickness or for the outer liner 20 to be configured to be thicker than the inner liner 10.

The outer liner 20 is fixed to the inner liner 10 in a distal end region 21, thereby forming a connection zone 21, in which the outer line 20 is firmly connected at an inner side to the outer side 16 of the inner liner 10. The connection may be established by way of sticking, welding, point-by-point connection or curing; a single-piece design may be achieved by way of a casting procedure during the primary forming process. Alongside a single-piece design, it is possible to first produce the inner liner 10 and the outer liner 20 separately from one another, and then to connect them to one another in a positive-locking or bonded manner. In the example of an embodiment shown, the inner liner 10 and the outer line 20 both feature a closed distal end region 11, 22. It is also possible that only one of the two liners 10, 20 has a distal end cap 12.

Both liners 10, 20 comprise at least one elastomer material component, wherein at least the outer liner 20 features an essentially airtight coating on its outer side 26 or the entire outer liner 20 is made of an airtight material.

Figure 2:
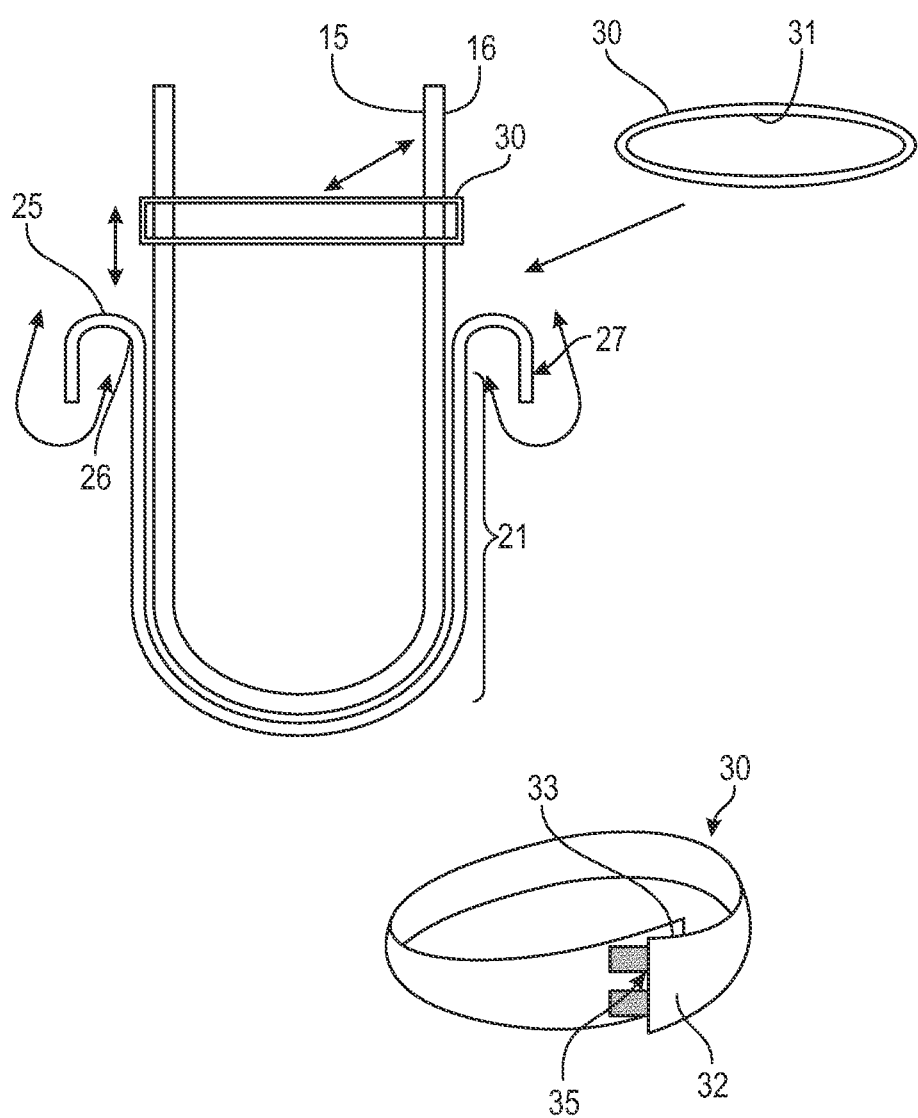
FIG. 2—a liner system according to FIG. 1 with an applied sealing element and a folded-down outer liner.
Figure 3:
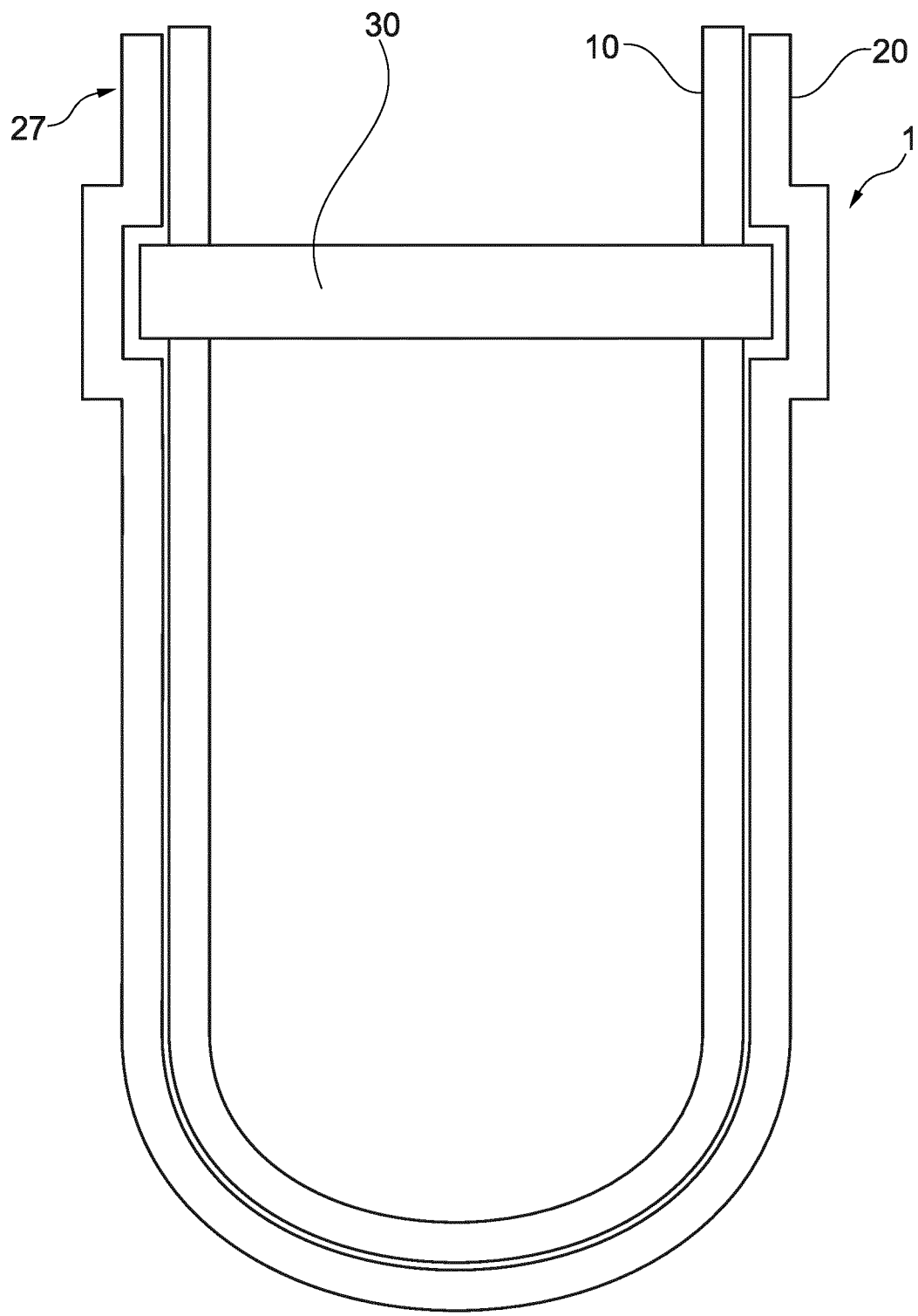
FIG. 3—a fully mounted liner system.

FIG. 2 shows the prosthetic liner system 1 during application. The inner liner 10 has already been applied to the stump of limb, not depicted. The outer liner 20 is pulled down or unrolled from its proximal end, i.e. from the entry opening, towards the distal end region 22, down to the proximal end of the connection zone 21, such that the actual inner side 25 of the outer liner 20 faces outwards. A separate sealing element 30, which is designed to be ring-shaped in the example of an embodiment depicted, is positioned in the region of the desired height on the outer side 16 of the inner liner 10. The sealing element 30 is shown next to the two liners in an individual diagram to the right. In the example of an embodiment shown, the cross-section of the sealing element 30 is rectangular; in principle, other cross-sectional forms of the sealing element 20 are also possible. Generally speaking, it is also possible for the sealing element 30 to be designed to be belt-shaped and placed around the inner liner 10 in order to apply it; this type of design of the sealing element 30 is shown below the prosthetic liner system 1. The sealing element 30 features free ends 32, 33, wherein said free ends 32, 33 may overlap with one another and are arranged around the inner liner 10 such that they overlap with one another to form a circumferential thickening when mounted. In this case, in order to prevent an undesired material thickening, the free ends 32, 33 may taper towards the end, such that a generally uniform material thickness is ensured in the event of an overlap in the respective end region of the sealing element 30, which ensures a uniform outer circumference of the applied sealing element 30. The free end regions 32, 33 of a belt-shaped sealing element 30 can be fixed to one another via fixing elements 35 or fixing devices, for instance by hooking or sticking the end regions together.

The sealing element 30 is reversibly fixed to the outer side 16 of the inner socket and features an even contact surface 31 in order to guarantee a flat and secure application of the sealing element 30 to the outer side 16 of the inner liner 10. Preferably, the sealing element 30 is also designed to be elastic, so as to enable any fluctuations in volume in the stump and thus changes in volume and the outer circumference of the inner socket 10 to be followed.

Following the application of the sealing element in the desired position on the inner liner 10, wherein the position can be set via markers on the inner liner 10 to facilitate a reproducible positioning of the sealing element for an end user, the outer liner 20 is rolled or pulled back up over the inner liner 10, such that the inner side 25 of the outer liner 20 lies flat, generally with its full surface, across the outer side 16 of the inner liner 10 and the sealing element 30. In the vicinity of the sealing element 30, the outer liner 20 bulges outwards and creates an enlargement in the circumference there, such that this area exhibits an increase in surface pressure upon the application of a prosthetic socket or other device, not depicted, in order to ensure a secure attachment there via a vacuum in the gap between the outer liner 20 and the prosthetic socket or socket, not depicted. When the liner system 1 is mounted, the separate sealing element 30, which can be attached reversibly and removed again, lies between the outer side 16 of the inner liner 10 and the inner side 25 of the outer liner 20. With the liner system 1, it is possible to cater for a multitude of patients with just one type of liner and to conduct a simple adjustment to different socket systems or sleeve systems. The location of the seal between the outer side of the liner and the inner side of the socket can be freely selected by way of the variable positioning of the sealing element 30 between the inner liner 10 and the outer liner 20 and individually optimized in consideration of the anatomical factors and structural design of the socket. The found, optimized position and course of the sealing line can be amended via the reversible arrangement of the sealing element 30, wherein the position of the sealing line can be selected by way of the positioning of the sealing element 30 in relation to the inner liner 10; said position can even be selected arbitrarily by way of an inclined positioning in relation to the longitudinal direction. Changes in volume over the course of wear of the socket can be compensated for by adjusting the sealing element 30. To achieve this, a multitude of sealing elements, which are easy to produce and cost-effective, with different dimensions, different cross-sections and in different materials can be kept on hand, said sealing elements rendering it easier to customize the liner system.

A permanent fixing of the outer liner 20 to the inner liner 10 facilitates the application of the liner system 1. In principle, it is also possible for the outer liner 10 and the inner liner 20 to be designed to be separate. It is possible for the inner liner 10 and the outer liner 10 to be designed to be identical, which would further reduce the production costs of the liner system 1.

Figure 4:
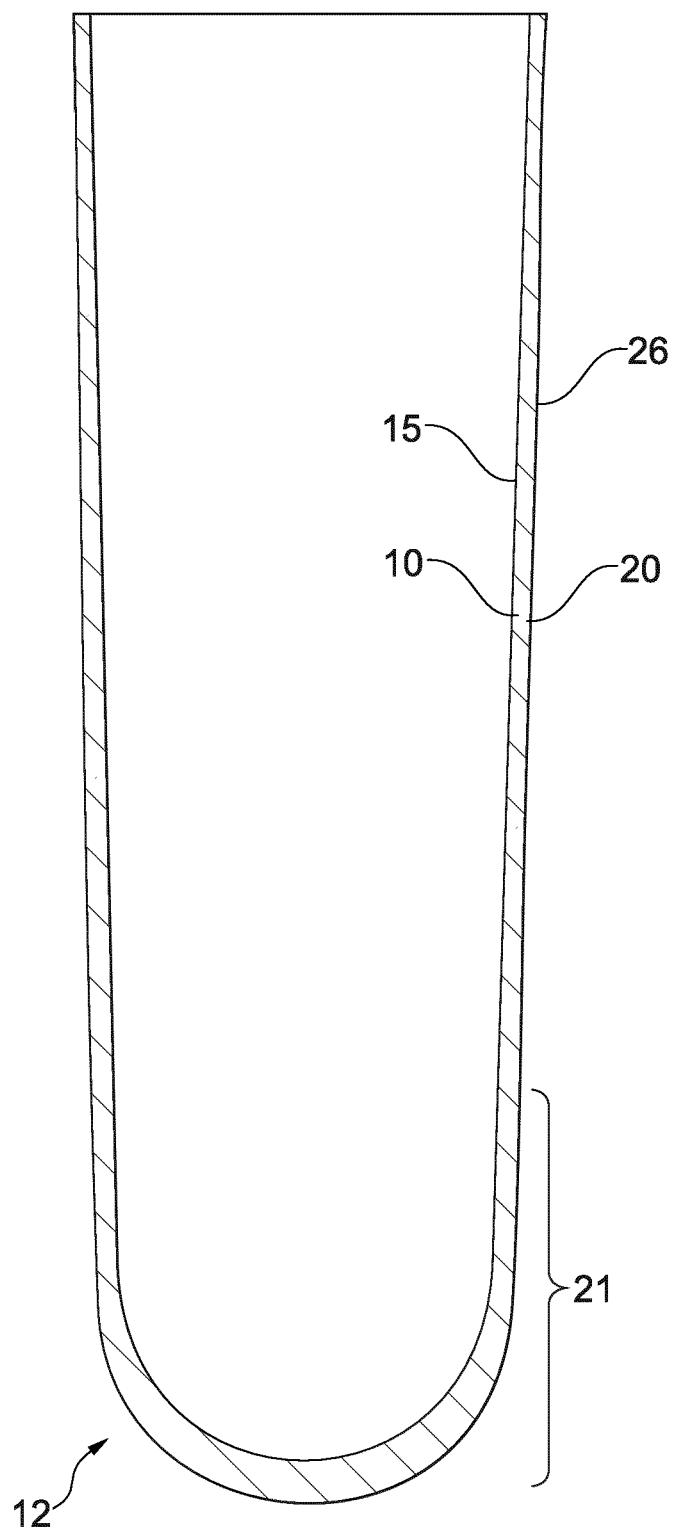
FIG. 4—a cross-sectional view of a liner system with no sealing element featuring a single-piece connection zone.

FIG. 4 depicts a cross-sectional view of a part of a liner system 1 with an inner liner 10 and an outer liner 20, which are designed in a connection zone 21 in the distal end region with a closed end cap 12, wherein the inner liner 10 and the outer liner 20 are connected by way of bonding in the connection zone 21 by means of a single-piece design. The connection zone 21 extends across between 25% and 30% of the total length of the liners 10, 20 in the initial configuration. The proximal end of the liner system 1 can be shortened if necessary. The liner 10 and the outer liner 20 are thus only partially separated from one another across the length of the liners 10, 20, for example via a corresponding device during production.

Figure 5:
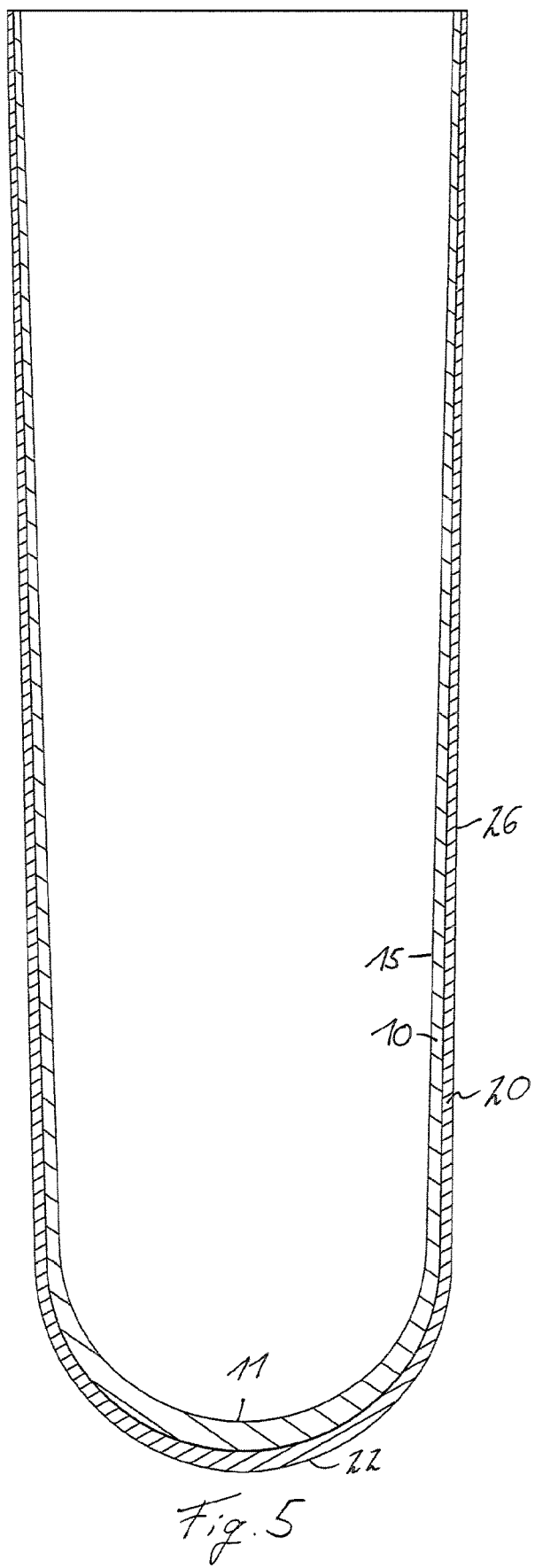
FIG. 5—a cross-sectional view of a liner system with no sealing element featuring two separate liners.

A variation of the invention is shown in a cross-sectional diagram in FIG. 5, in which the inner liner 10 and the outer liner 20 are produced as separate liners and applied adjacent to one another. Where appropriate, there may be a connection between the outer liner 20 and the inner liner 10 in the distal end regions 11, 20, for instance by gluing sections of said liners or via fixing elements, such as positive-locking elements, e.g. hook and loop sections.

Figure 6:
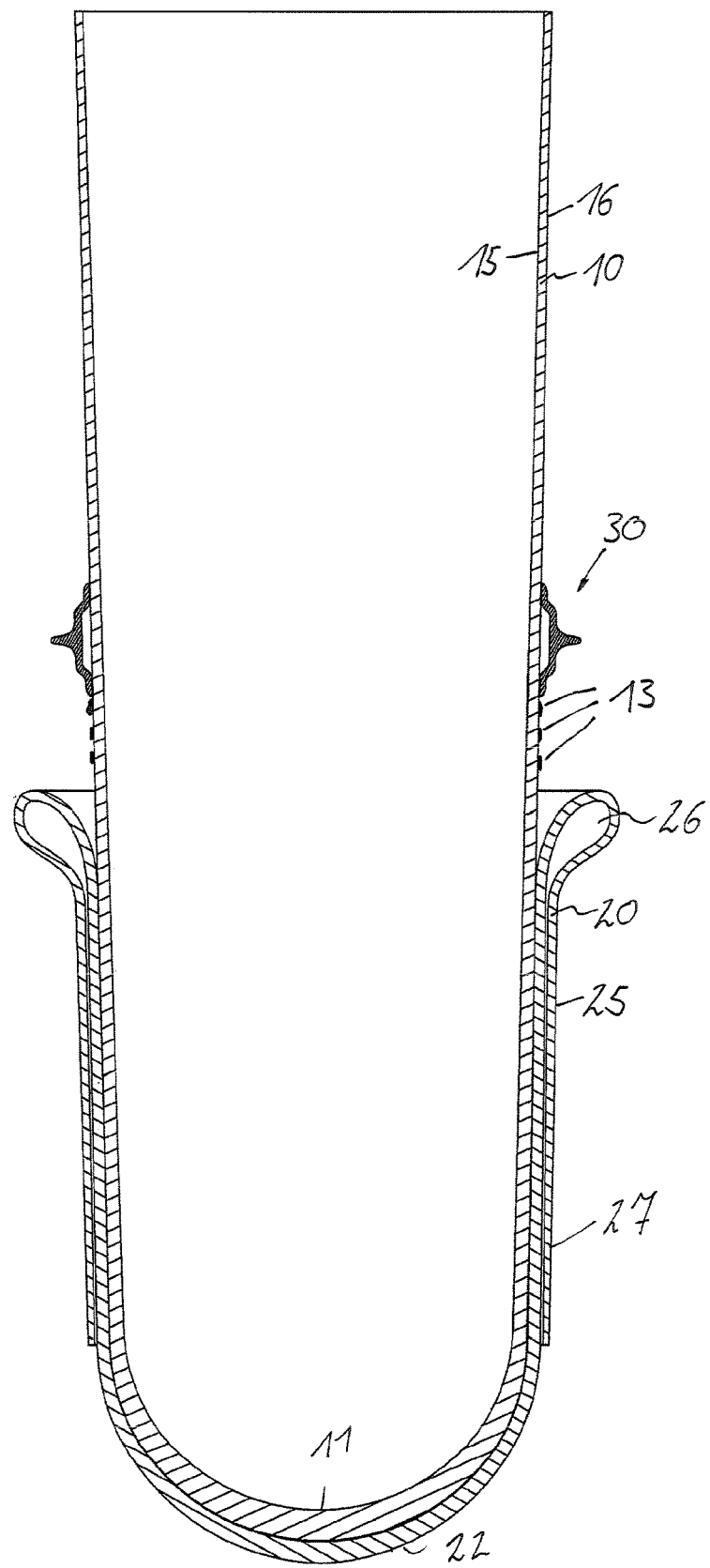
FIG. 6—a variation of FIG. 2.
Figure 7:
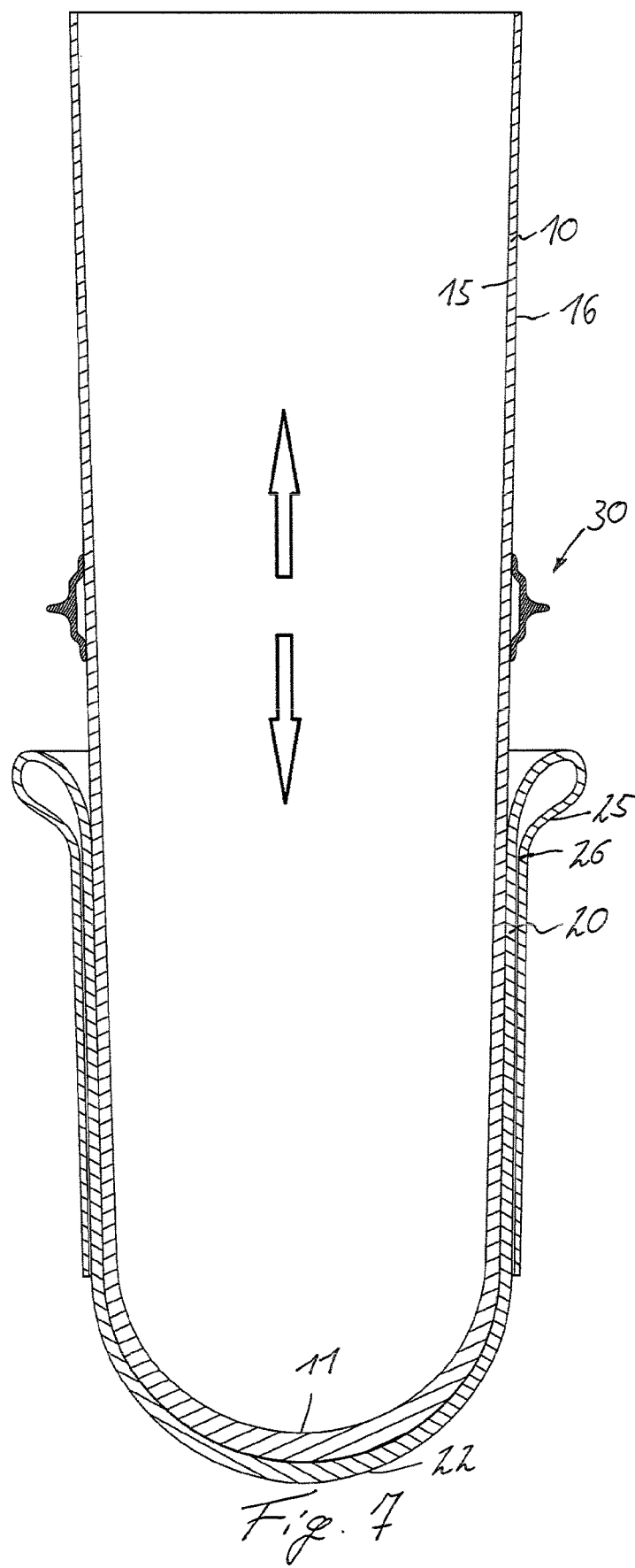
FIG. 7—a diagram of the moveability of the sealing element on the inner liner.

In a cross-sectional view, FIG. 6 depicts a variation of FIG. 2, in which an inner liner 10 and an outer liner 20 are joined together, in a similar manner to the depiction in FIG. 5, such that the outer side 16 of the inner liner lies flat on the inner side 25 of the outer liner 20. The proximal end 27 or a proximal end region 27 of the outer liner 20 is pulled down from the proximal end towards the distal end region 22, thereby exposing the outer side 16 of the inner liner 10. The inner side 25 of the outer liner 20 has been partially turned inside out. A ring-shaped sealing element 30 is arranged on the outer side 16 of the inner liner 10, said sealing element comprising two contact surfaces which are situated at a distance from one another in the longitudinal direction of the inner liner 10. A tongue, which faces radially outwards, is circumferentially configured on the sealing element 30. The sealing element 30 may be adhesively attached and fixed on the outer side 16 of the inner liner 10 via an elastic holding force, which is exerted as a result of an elastic design of the ring-shaped sealing element 30, or via an adhesive connection. If there is no adhesive fixing of the sealing element 30 to the outer side 16 of the inner liner 10, the sealing element 30 can be displaced along the longitudinal direction of the inner liner 10, wherein this occurs on the outer side 16 of said inner liner, as indicated by the double arrow in FIG. 7. The position of the sealing element 30 on the inner liner 10 can thus be freely selected; an adjustment can be made to fit the needs of the respective patient, in coordination with an orthopedic technician. Once found, a position of the sealing element 30 on the inner liner 10 that is deemed comfortable or optimal can be recorded by a marker. Markers 13 may be configured, applied or incorporated on the outer side 16 of the inner liner 10 to enable a simple reversible attachment of the separate sealing element 30 on the inner liner 10. The markers are shown in a circumferential pattern in FIG. 6; however, they may also simply be arranged along one or several lines that run in the longitudinal direction of the inner liner 10. The markers 13 may be arranged on the outer side 16, the inner side 15 or inside of the inner liner 10. It is also proposed that circumferential markers 13 do not run perpendicular to the longitudinal direction of the inner liner 10.

Figure 8:
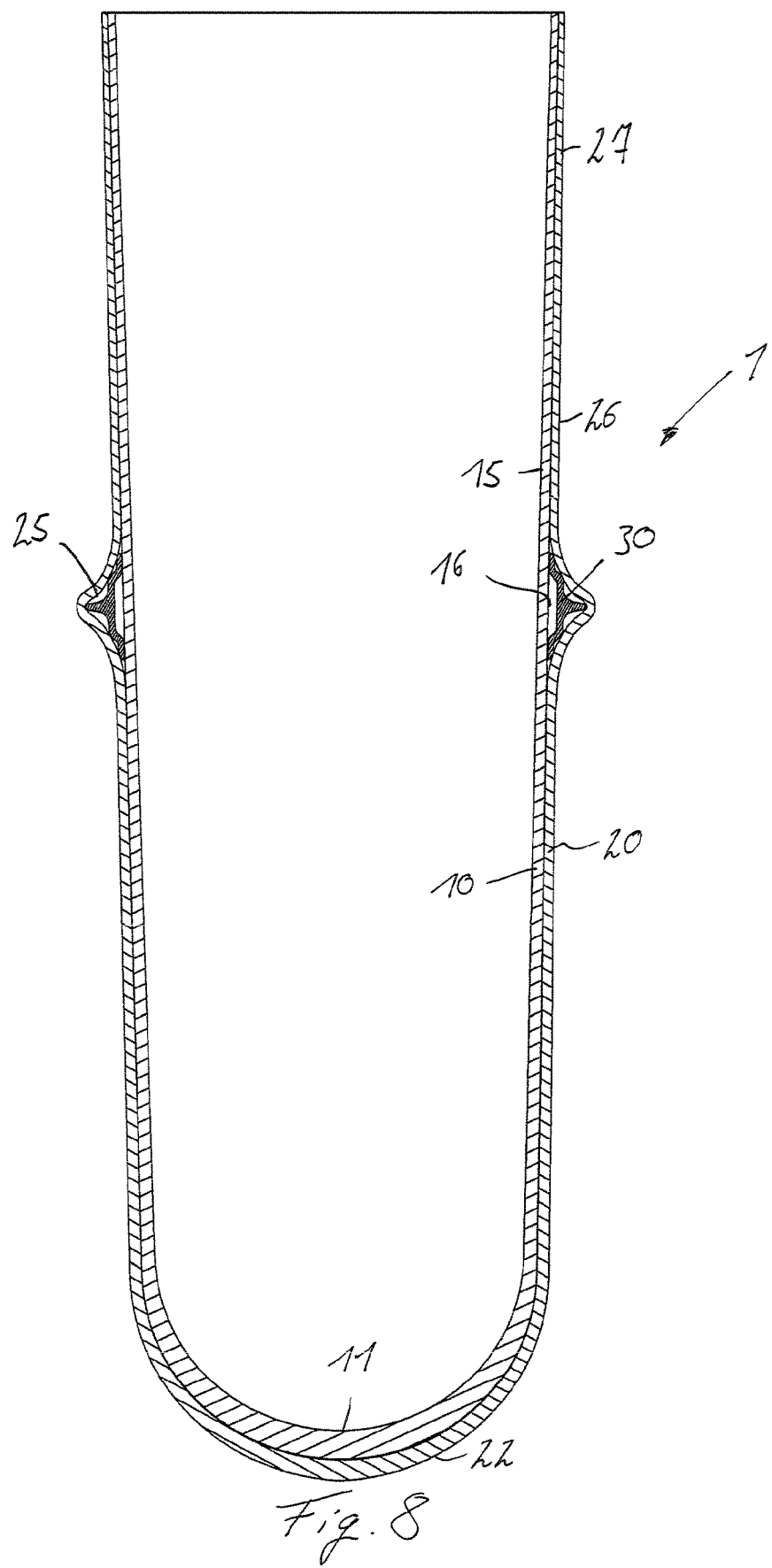
FIG. 8—a cross-sectional view of a fully mounted liner system.

FIG. 8 depicts a fully mounted liner system that has not been applied on a stump. The proximal end 27 of the outer liner 20 is once again folded upwards, such that the inner side 25 of the outer liner 20 lies flat on the outer side 16 of the inner liner 10. The outer liner 20 covers the sealing element 30, wherein a bulge forms inside of the outer liner 20 in the vicinity of the sealing element 30 by way of the tongue of the sealing element 30, which faces radially outwards. If such a liner system 1 with an inner liner 10, an outer liner 20 and a separately produced sealing element 30 arranged between them is inserted into a dimensionally stable prosthetic socket, not depicted, an increase in contact pressure of the outer liner 20 on the inner wall of the prosthetic socket occurs in the vicinity of the sealing element 30, such that the outer side 26 of the outer liner 20 lies on the inner circumference of the prosthetic socket such that it produces a sealing effect. The liners 10, 20 are preferably made of an elastomer material, especially an airtight elastomer material.

Figure 9:
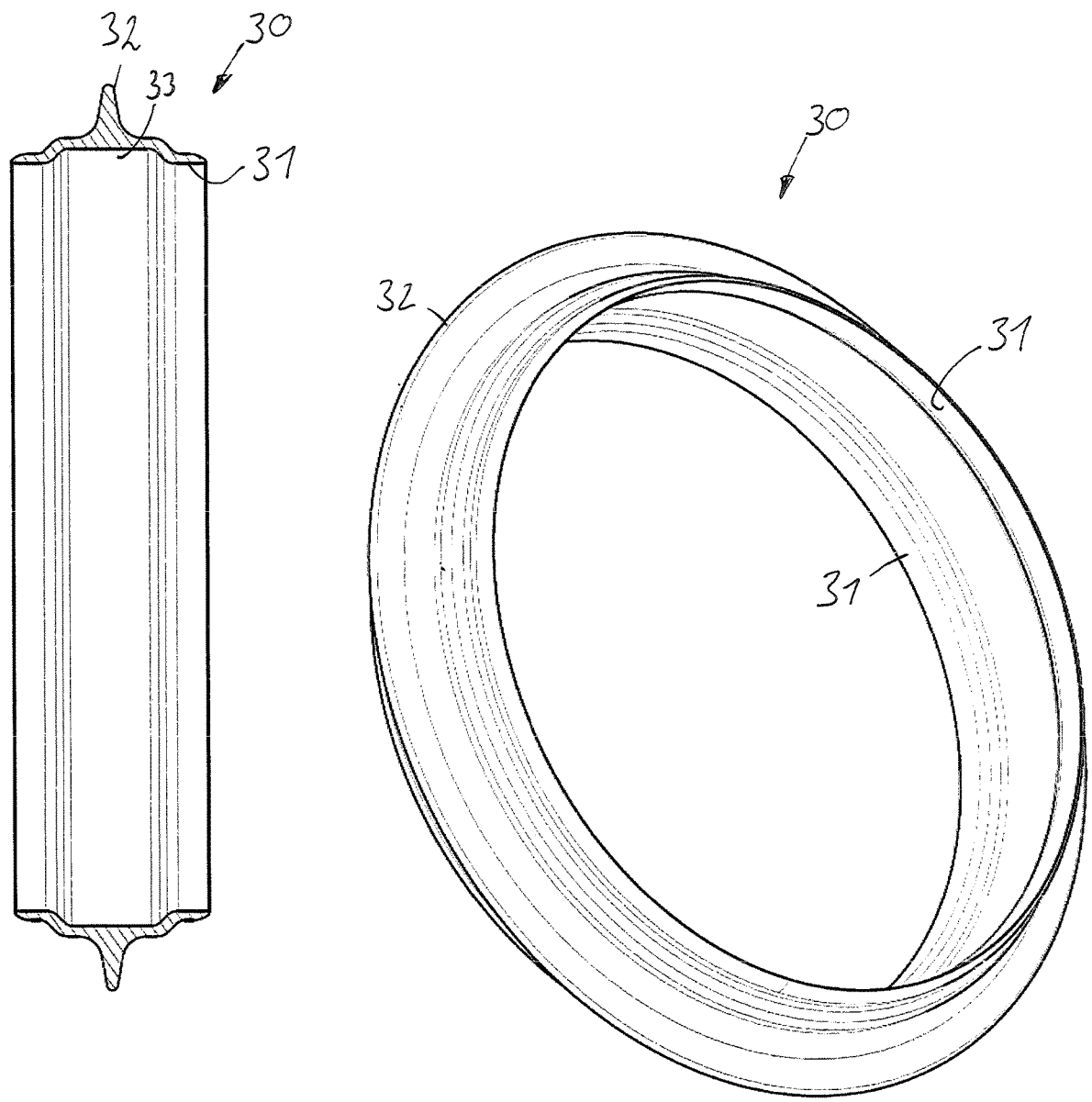
FIG. 9—a diagram of a sealing element in a perspective view and a cross-sectional view.

FIG. 9 shows an individual diagram of the sealing element 30 according to FIG. 8 in both a perspective view and a cross-sectional view. The sealing element 30 is designed to be ring-shaped and, in addition to two largely cylindrical, smooth contact surfaces 31, comprises a circumferential tongue 32 that faces outwards. A step and a free space 33 are devised between the two contact surfaces 31, which are situated at a distance from one another, wherein said step and free space are intended to enable an elastic deflection of the tongue 32 towards the flat contact surfaces 31. The free space 33 also allows for a solely partial deflection of the tongue 32 radially inwards, specifically if the sealing element 30 is made of an elastomer material. The contact surfaces 31 can be designed to be adhesive or be equipped with an adhesive coating. The tongue 32, which faces radially outwards, may feature a greater degree of dimensional stability compared to the rest of the material. The tongue 32 may be designed to be flexible, especially elastic, so that it deforms following the application of the outer liner 20 or the insertion of the liner system into a socket; in particular, it fits closely to the inner liner 10.

Figure 10:
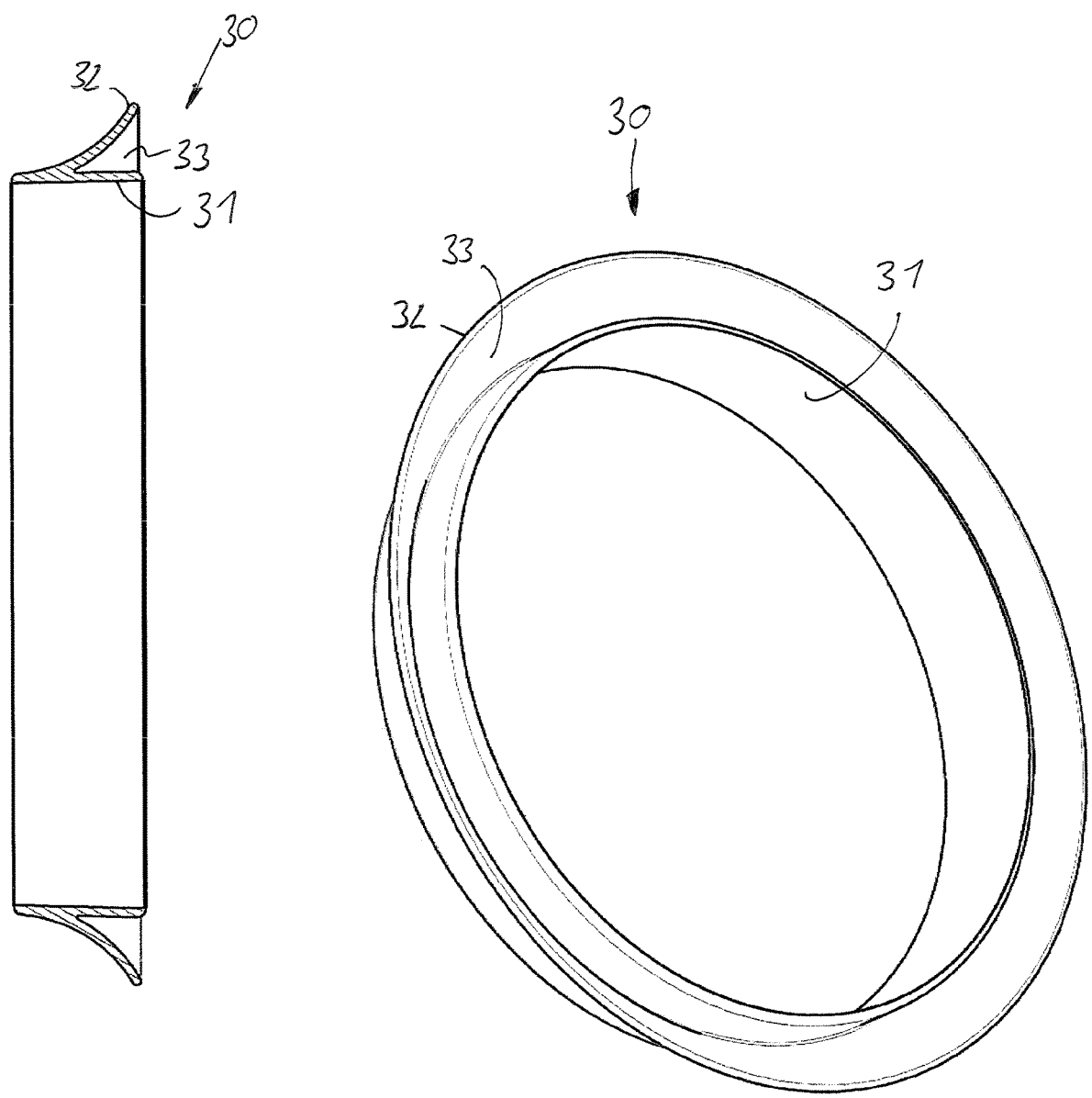
FIG. 10—a variation of a sealing element.

A variation of the sealing element 30 is shown in FIG. 10 in a perspective diagram and a cross-sectional diagram. The contact surface 31 is designed to be a flush surface, so that a ring or a base body forms from which a circumferential tongue 32 extends radially outwards in a curve. A free space 33 is formed by an outer edge of the circumferential tongue 32 up to the circumferential ring, on whose inner side the contact surface 31 is configured, said free space enabling a radially inward deflection of the outer edge of the circumferential tongue 32.

Figure 11:
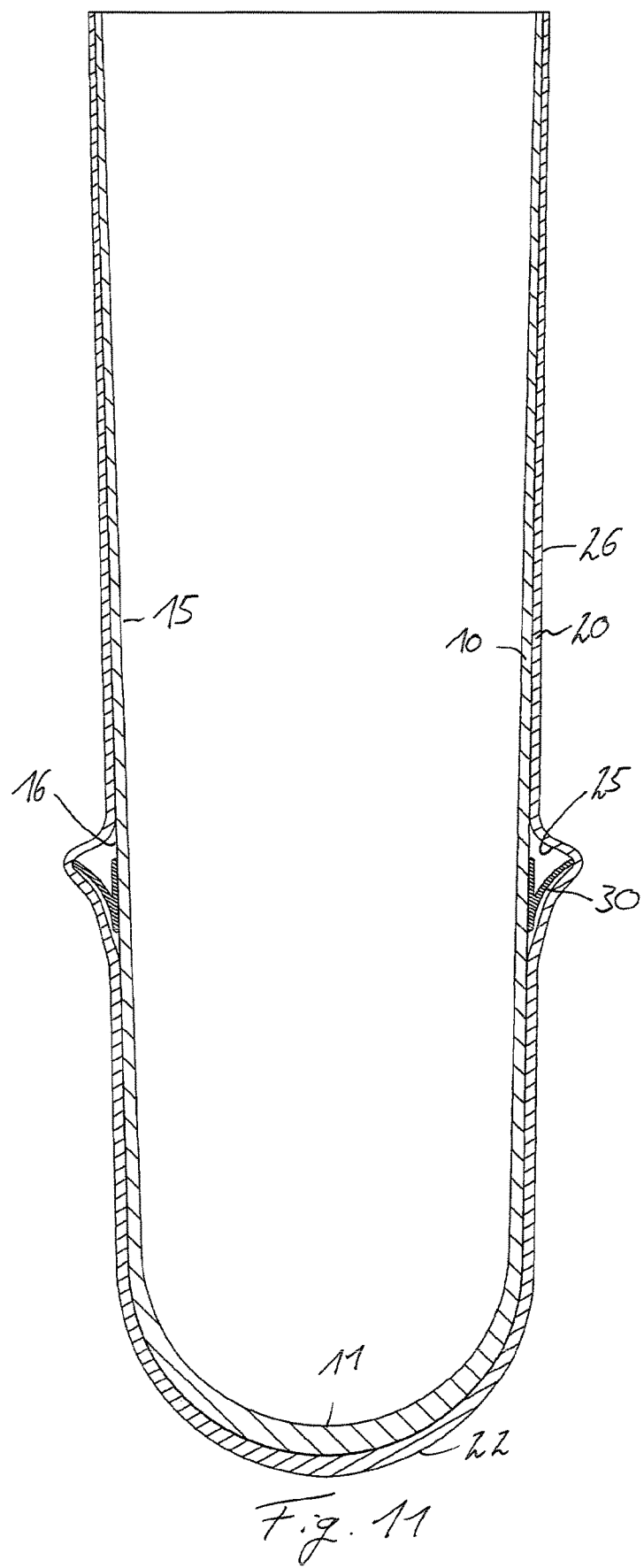
FIG. 11—a fully mounted liner system with a sealing element according to FIG. 10.

The mounted liner system 1 with a sealing element 30 according to FIG. 10 is shown in FIG. 11. The sealing element 30 is mounted in such a way that a V-shaped design occurs, which widens towards the proximal end, such that, upon an insertion of the liner system 1 into a prosthetic socket, the outer lip or tongue 32 can be pushed radially inwards, wherein the lip or tongue 32 can be moved into the free space 33 and an elastic restoring force is exerted, which acts outwards. The lip or tongue 32 and the base body with the contact surface 31 are either connected to one another or configured as a single-piece.

Figure 12:
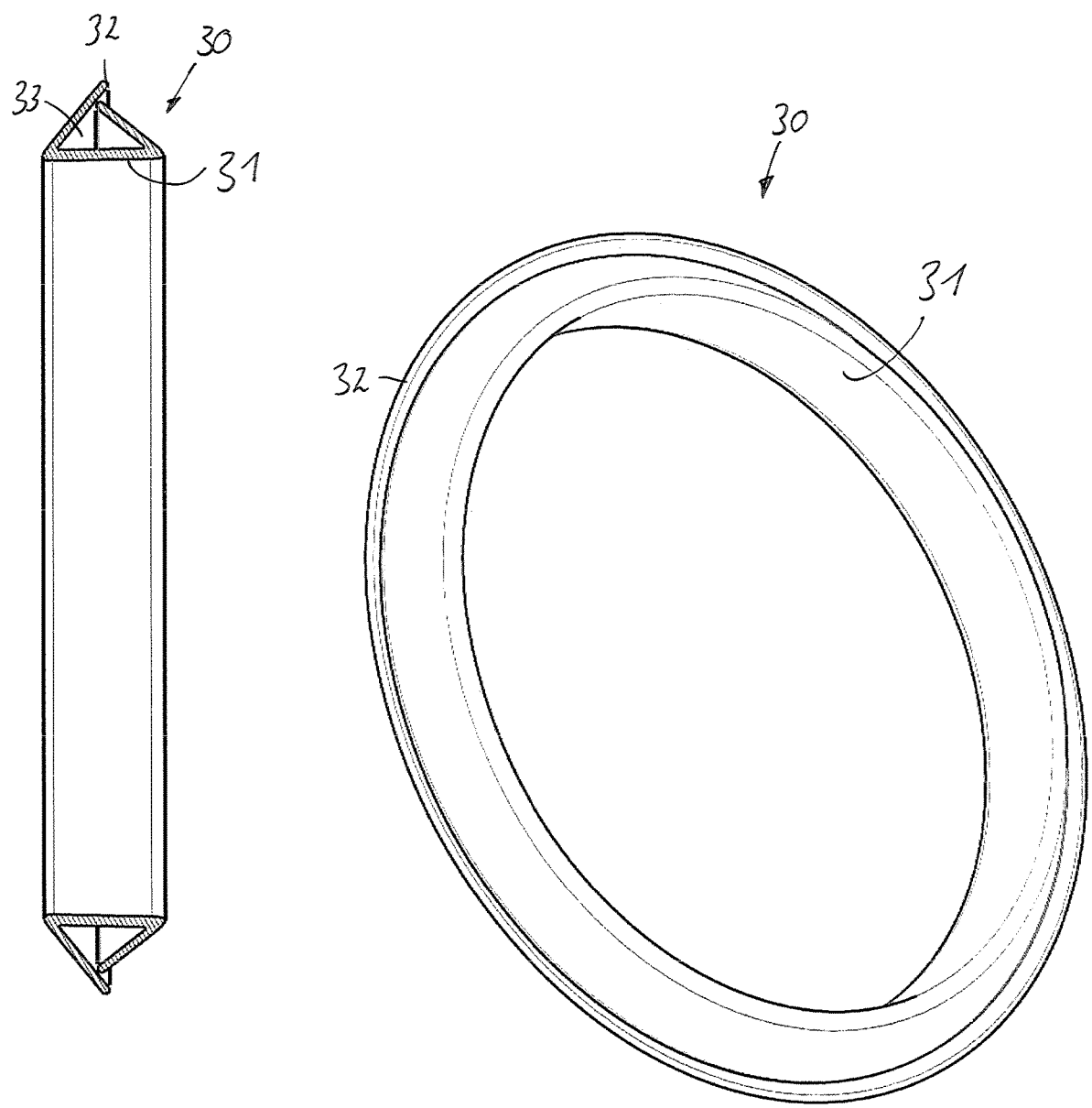
FIG. 12—a separate sealing element in a perspective view and a sectional view.

FIG. 12 shows a variation of the sealing element 30 with a generally triangular cross-section, as depicted in the left-hand diagram in FIG. 12. A belt-shaped base surface with a flat contact surface 31 configured on the inner side serves the attachment to the outer side 16 of the inner liner 10. Two arms extend towards one another from the base side in such a way that a hollow space 33 forms, the cross-section of said space been essentially triangular. In the embodiment depicted, the left arm is longer than the right arm, resulting in an overhang that forms an outer edge or tongue 32. As a result of the hollow space 33 and the fact that the two arms, which protrude towards one another from the base side, are not connected to one another, a radially inward displacement may occur in the event of compression and a pressure from outside acting towards the base side of contact surface 31.

Figure 13:
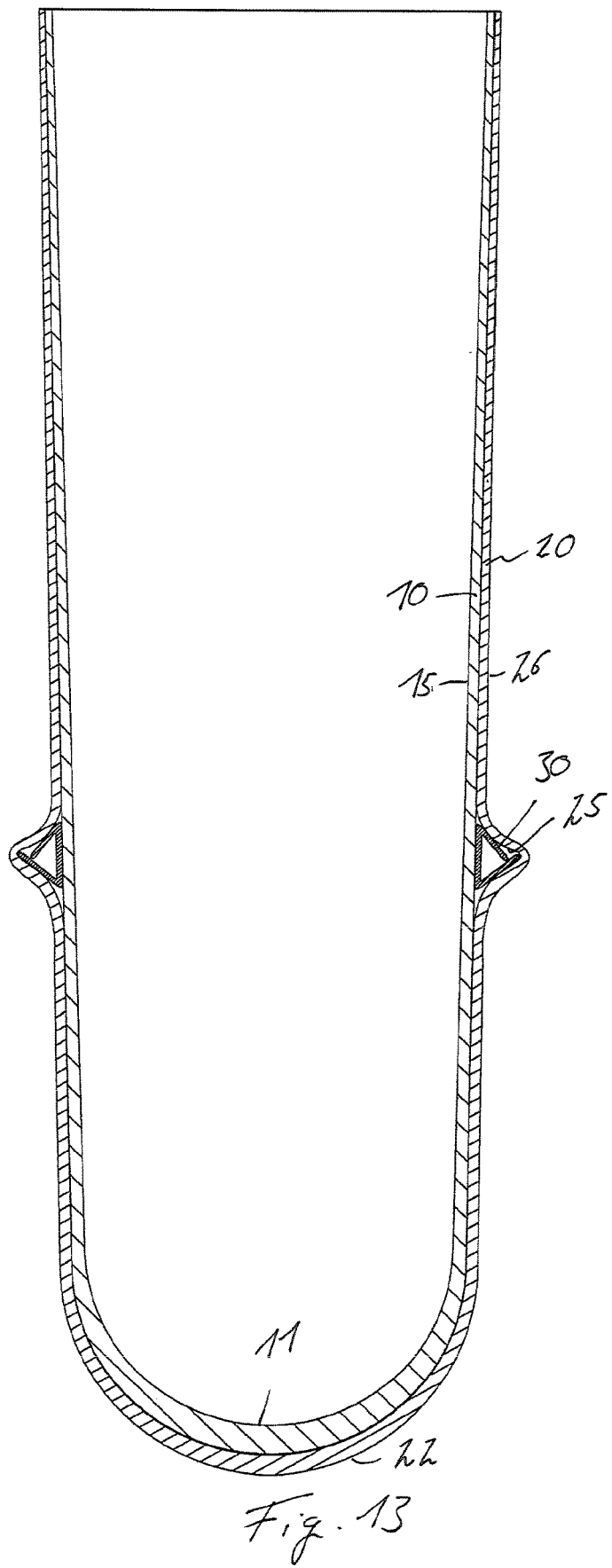
FIG. 13—a fully mounted liner system with a sealing element according to FIG. 12.

The fully mounted liner system 1 is depicted in FIG. 13, in which the sealing element 30 is arranged according to FIG. 12 between the inner liner 10 and the outer liner 20.

Figure 14:
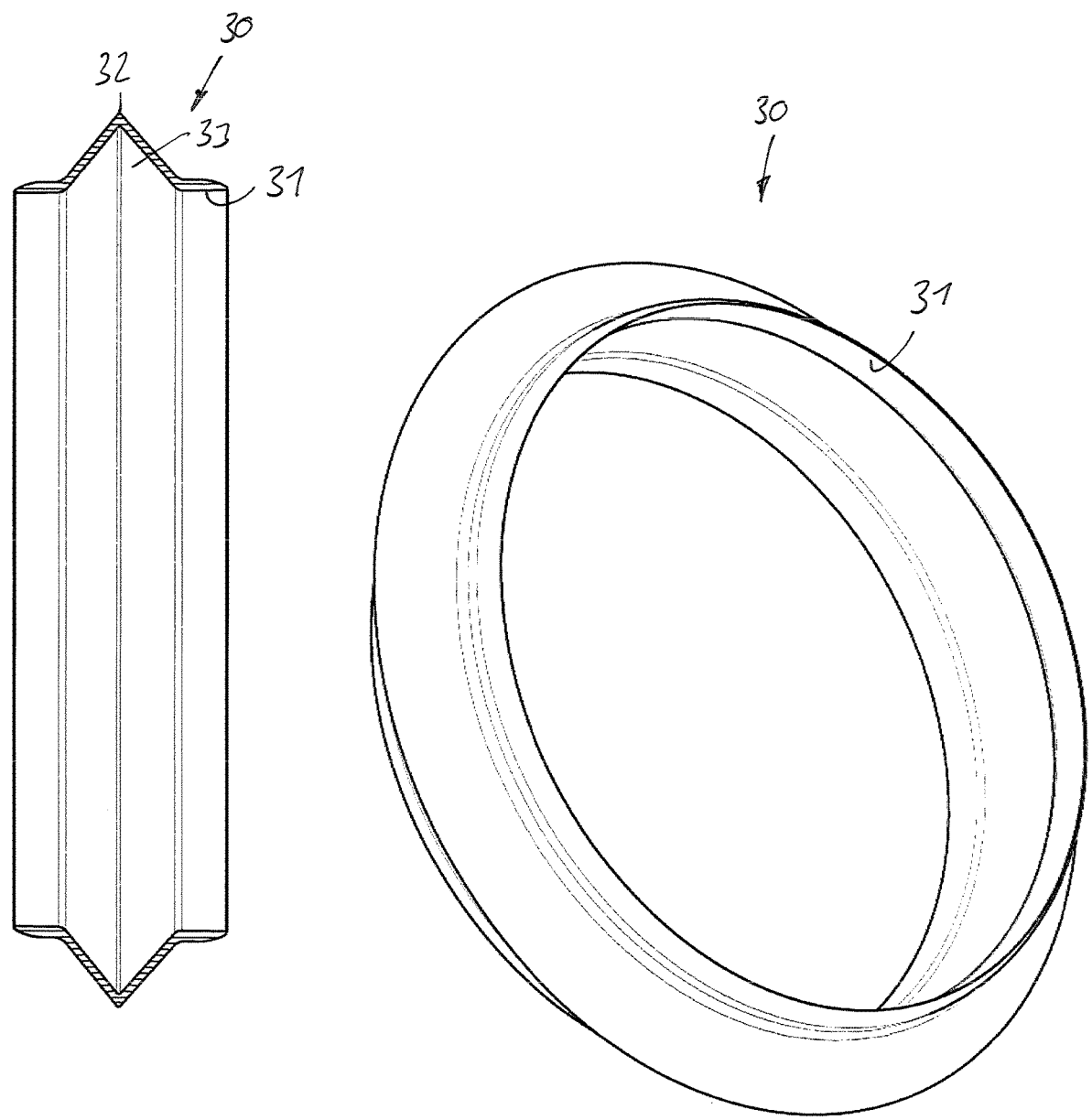
FIG. 14—a variation of the sealing element.
Figure 15:
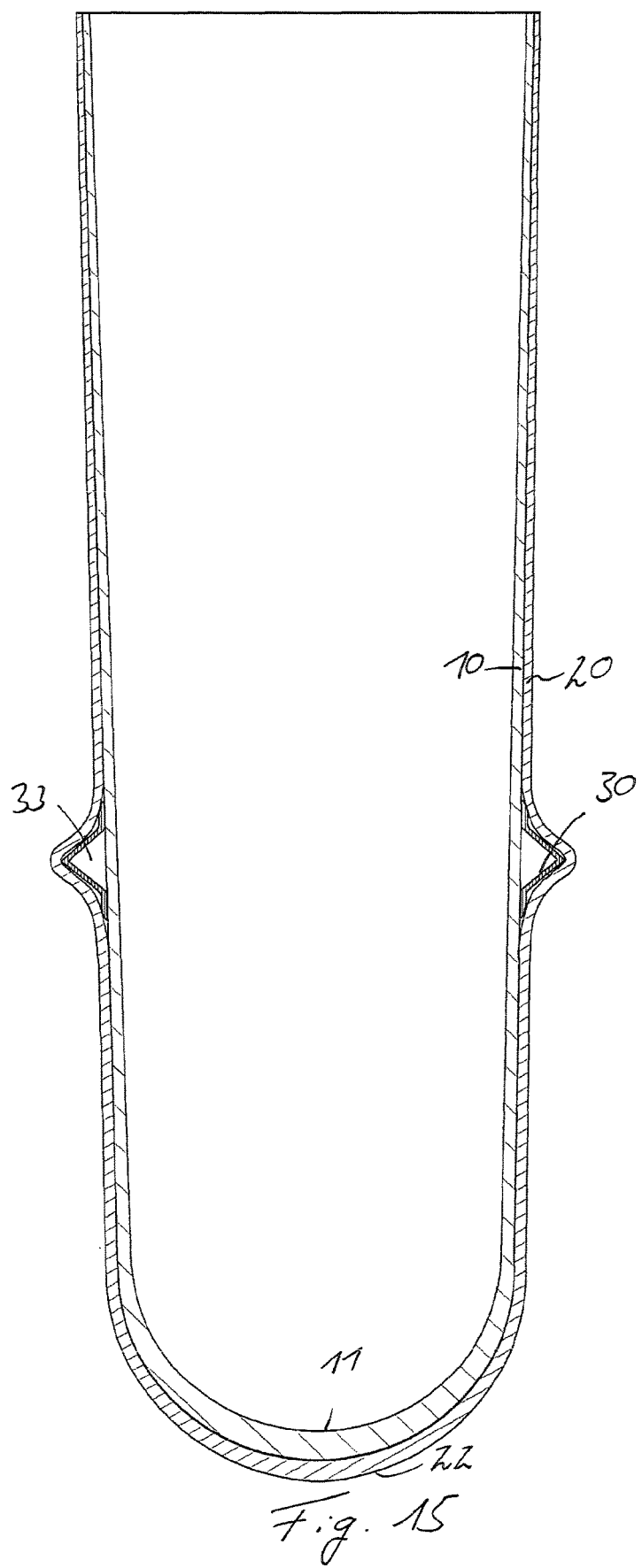
FIG. 15—a fully mounted liner system with a sealing element according to FIG. 14.

Another variation of the invention is depicted in FIG. 14, in which the sealing element comprises two contact surfaces 31, as in FIG. 9, from which two conical arms extend radially outwards at an angle, such that a circumferential edge or a radially protruding tongue 32 is formed. The conical design results in a hollow space 33 between the contact surfaces 31 and a generally pointed, triangular configuration of the sealing element 30 when mounted. The fully mounted liner system 1 is visible in FIG. 15, wherein the hollow space 33 of said liner system is generally triangular when mounted. The outer circumferential edge or tongue 32 of the conical edges results in the formation of a bulge of the outer liner 20 in the vicinity of the sealing element 30.

Figure 16:
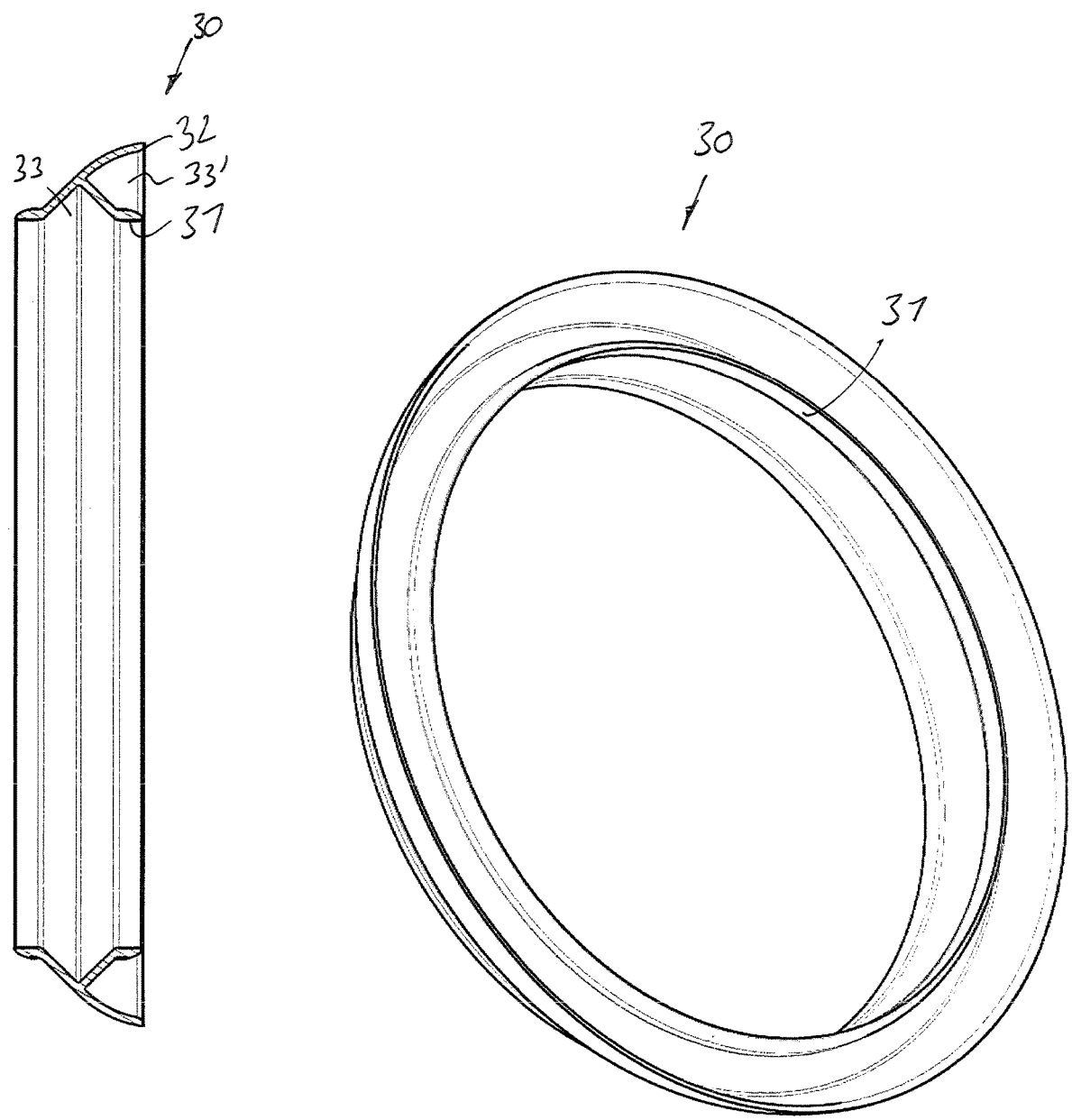
FIGS. 16 and 17—individual views of a sealing element in a perspective view and a cross-sectional view.

Another variation of the sealing element 30 is shown in FIG. 16, in which a first triangular hollow space 33 is formed between the contact surfaces 31, in a similar manner to the form according to FIG. 14. In the area around the roof-like connection point of the two conical edges, another tongue 32 extends towards a side of the sealing element 30, such that a second hollow space 33' forms between a first contact surface 31 and the outer edge 32. This type of configuration allows for a multiple deflection of the sealing element 30 in the radial direction.

Figure 17:
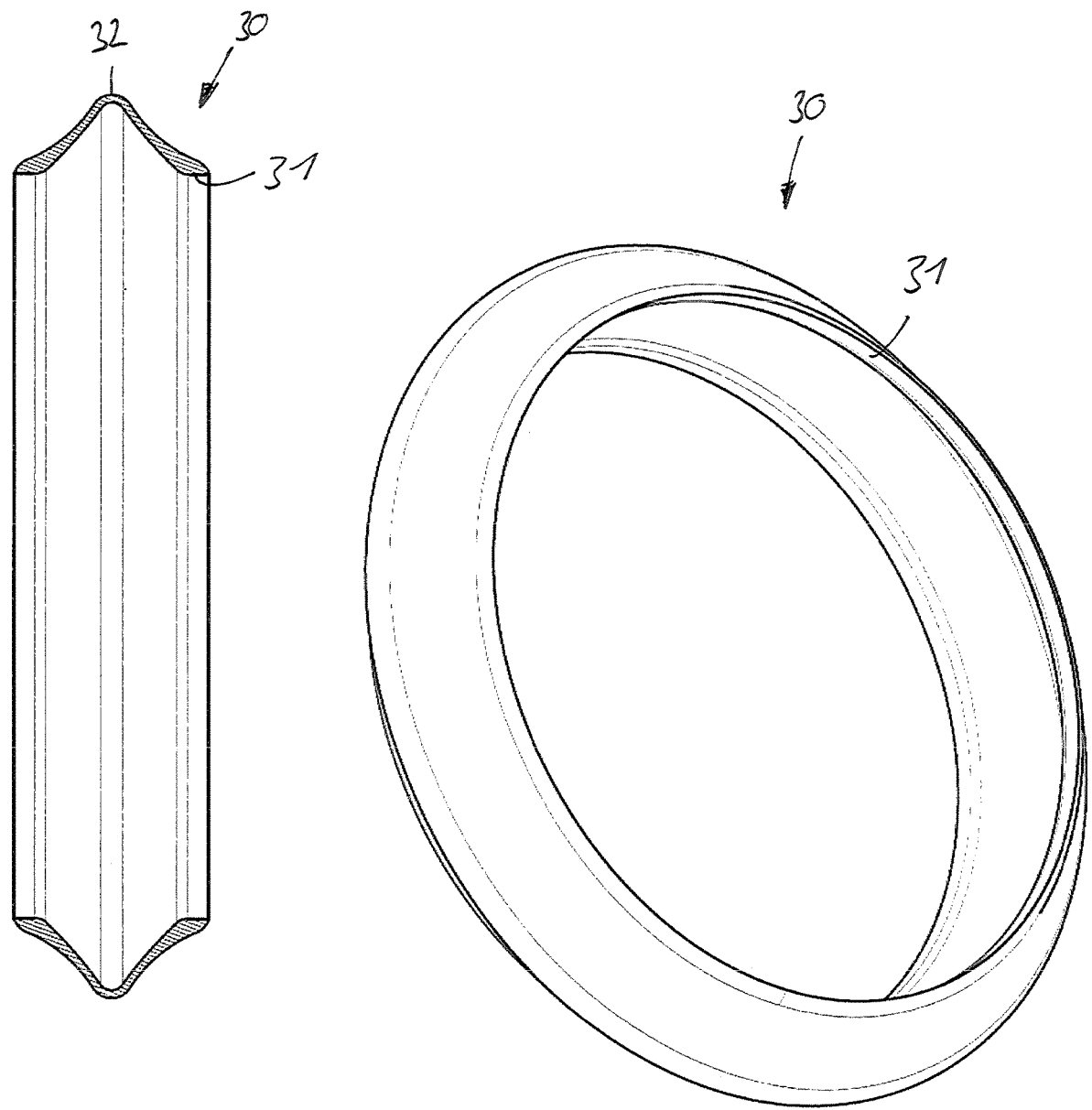

FIG. 17 shows another variation of the sealing element with a curved form. An arm extends, curved and roof-life, from each of the two contact surfaces 31 towards the outer circumference to form a projection or a tongue 32, which is also designed to be rounded. The rounded design of both the arms and the outer circumferential edge results in a rounded bulge of the outer liner 20 when in the fully mounted state.

Figure 18:
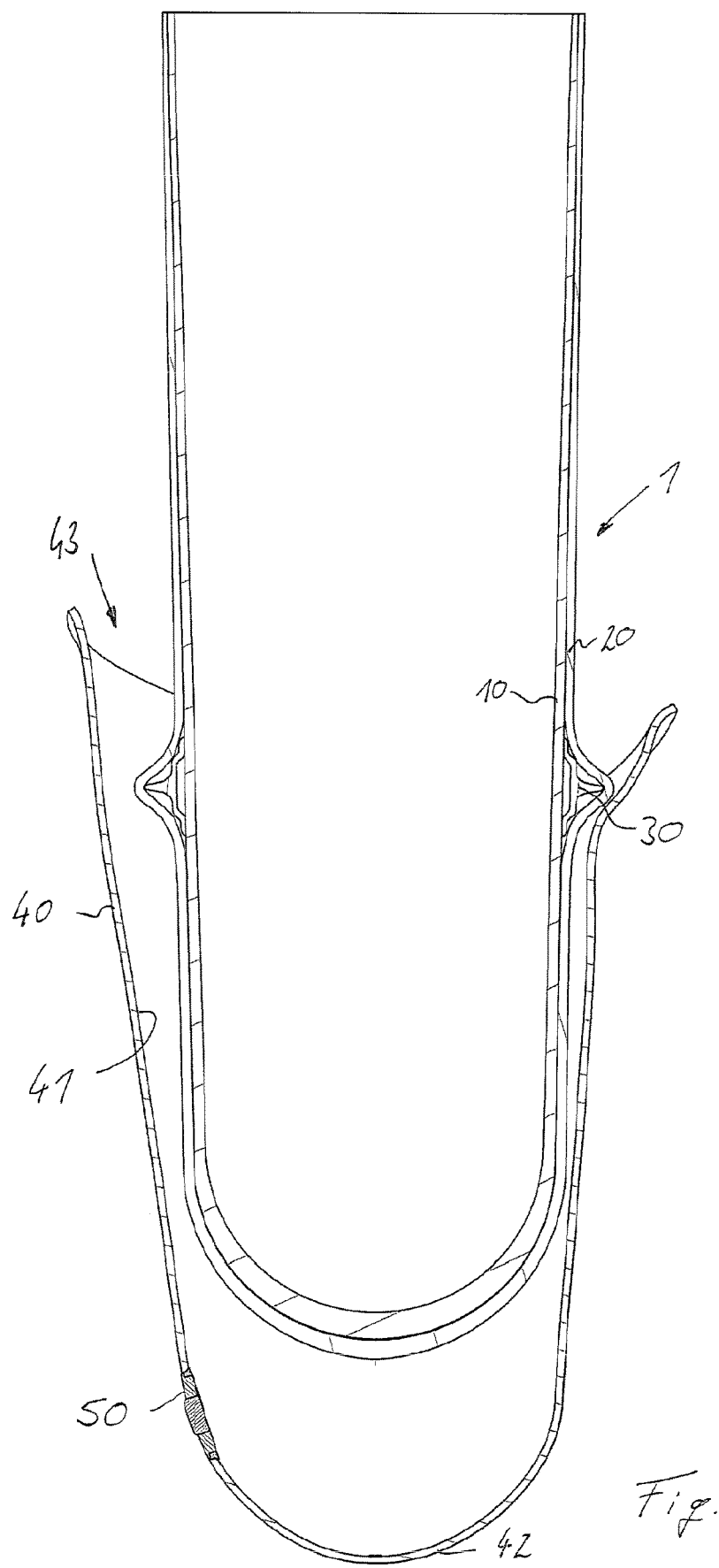
FIG. 18—a sectional view of a variation with a prosthetic socket.

In a schematic sectional diagram, FIG. 18 depicts a prosthetic liner system 1 with an inner liner 10 and an outer liner 20 as well as a sealing element 30 arranged between them. The structure is generally equivalent to the structure shown in FIG. 8, wherein the sealing element 30 is arranged at a further distal point than in FIG. 8. The prosthetic liner system 1 is partially inserted into a prosthetic socket 40, which comprises a closed distal end section 42 and a proximal insertion opening 43. The prosthetic socket 40 expands from the distal end section 42 to the proximal insertion opening 43, so that it is designed to expand in a generally conical manner. In the example of an embodiment shown, the prosthetic socket 40 features a closed inner wall 41 and is made of a dimensionally stable material, such as a fiber-reinforced plastic, an alloy or a similarly stable and light material. Fixing devices for further prosthetic components can be arranged on the outer side of the prosthetic socket 40 for the attachment of said prosthetic components to the prosthetic socket 40, for instance accommodation components for connecting adapters, connecting adapters in and of themselves, laminated connecting adapters or laminated fixing devices such as screw holes, bolts or mounting plates, in order to fix frames, rails or prosthetic joints directly to them, in particular prosthetic knee joints or prosthetic elbow joints, prosthetic ankle joints or prosthetic wrist joints. In principle, other prosthetic components, such as prosthetic feet, lower leg tubes, lower arm tubes or similar, can be fixed directly to the prosthetic socket 40.

In FIG. 18, the prosthetic liner system 1 is not fully inserted in the prosthetic socket 40, but rather initially abuts the inner wall 40 of the prosthetic socket in the vicinity of the proximal insertion opening 43 with the non-compressed, enlarged outer circumference of the outer liner 20, without it resulting in a complete application of the outer liner 20, which protrudes outwards in a curved manner. Due to the conical tapering of the prosthetic socket 40 towards the distal termination area 42, upon a further insertion of the liner system 1, the outer liner 20 will come into full contact with the inner side 41 of the prosthetic socket in the area around the largest bulge by way of the projection of the sealing lip 30, thereby forming a closed volume if the outer liner 20 lies fully on the prosthetic socket inner wall 41 in the area around the sealing lip 30, such that it has a sealing effect. If the liner system 1 is inserted further in the distal direction towards to distal termination area 42 of the prosthetic socket 40, the air enclosed in the volume is initially compressed. In this case, the sealing element 30, which is designed with a tongue 32 that faces vertically outwards in the example of an embodiment shown, is compressed on the one side and bent on the other, so that the tongue 32 is bent because of the conical shape of the prosthetic socket 40 and the insertion motion towards the proximal end of the liner system 1. During an increase in pressure upon stepping into the prosthetic socket 40, the air that is enclosed and compressed inside the volume may escape at the outer side of the sealing lip and the outer liner 20.

To prevent, on the one hand, unpleasant noises upon the lateral escape between the prosthetic socket inner wall 41 and the outer liner 20 and, on the other hand, to enable a stepping out of the prosthetic socket 40, a valve 50 is provided in the prosthetic socket wall, said valve serving to ventilate and aerate the gap between the outer liner 20 and the inner side 41 of the prosthetic socket 40. Upon stepping into the prosthetic socket, air is automatically pushed out of the closed volume between the prosthetic socket 40 and the outer side of the liner system 1. Should the patient wish to step out of the prosthetic socket 40, i.e. to pull the stump and the liner system 1 out in the proximal direction, the valve is activated manually, for instance, in such a way that air can flow into the gap, so that, in order to step out of or pull the liner system 1 out of the prosthetic socket, it is only necessary to overcome any remaining adhesive forces between the outer line 20 and the inner wall 41 of the prosthetic socket and elastic restoring forces via the sealing element 30.

Figure 19:
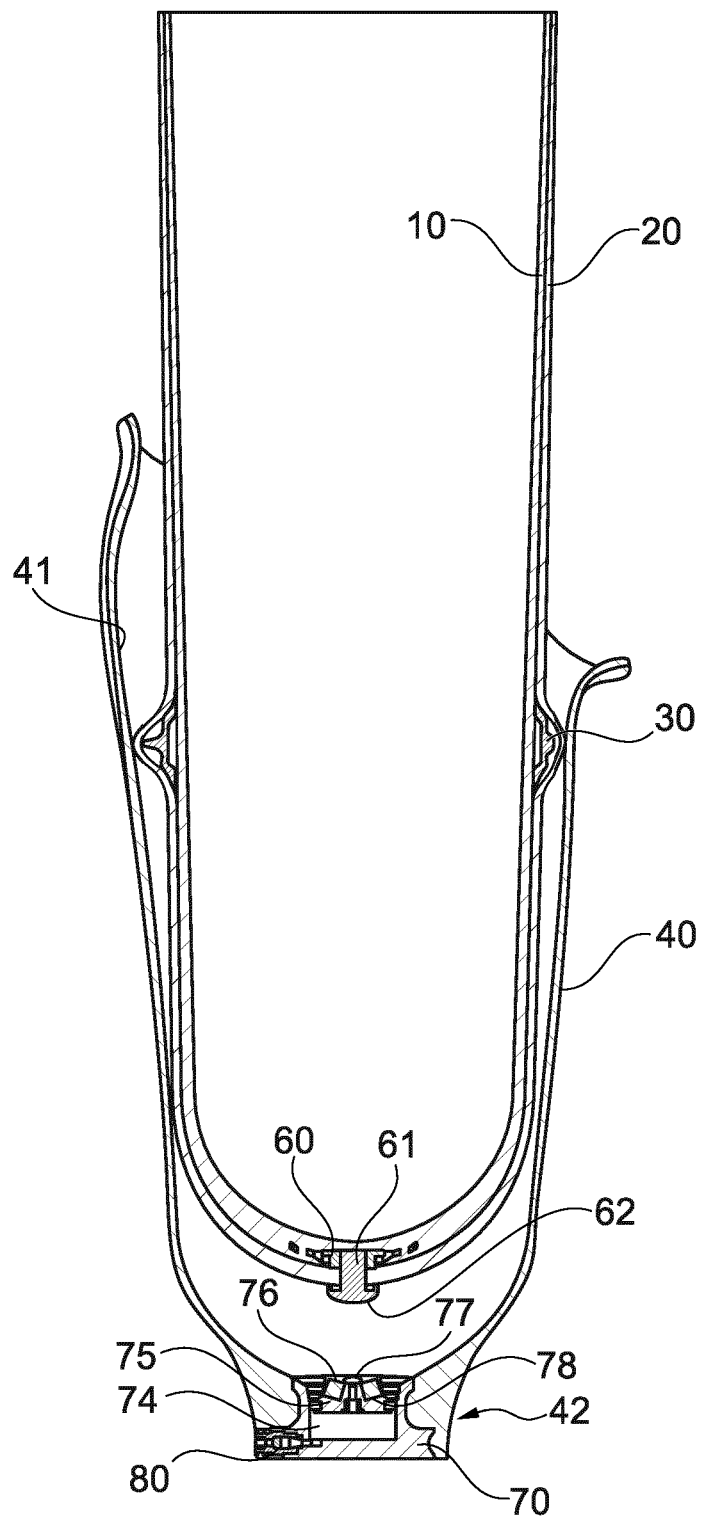
FIGS. 19 to 21—sectional views of an insertion movement of a liner system into a prosthetic socket.
Figure 20:
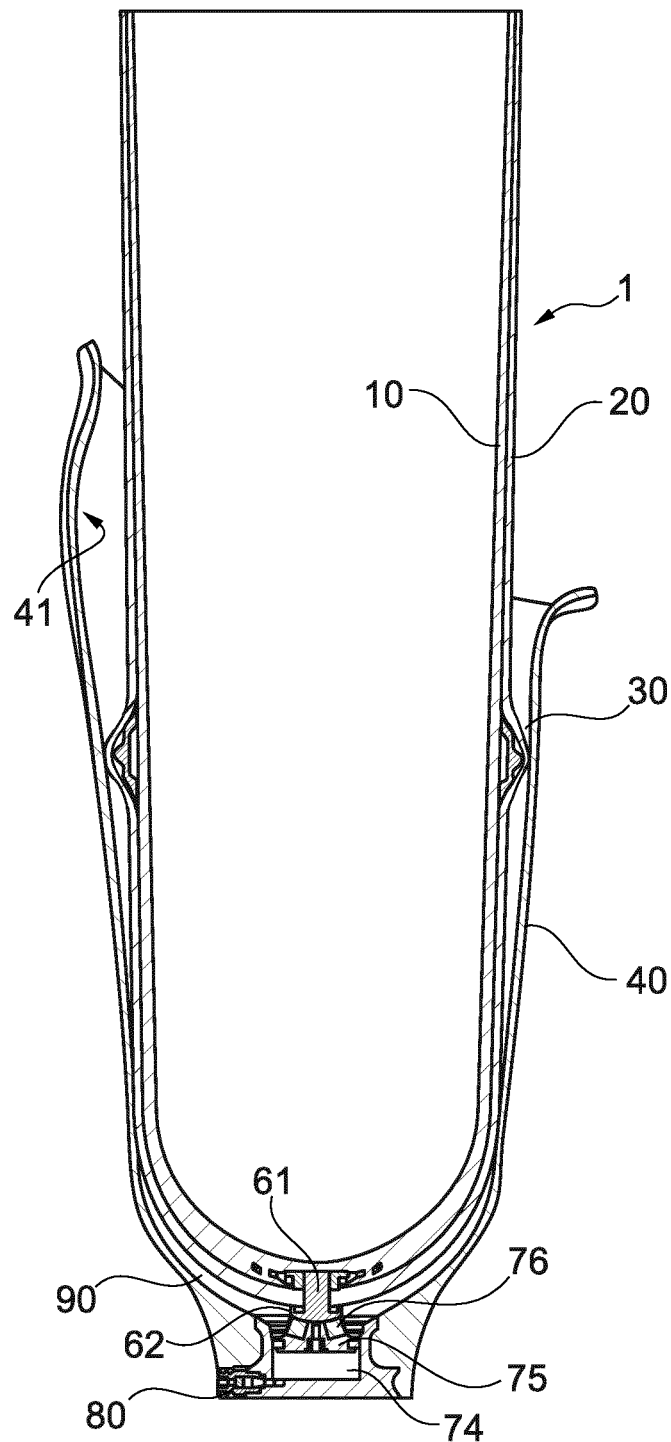
Figure 21:
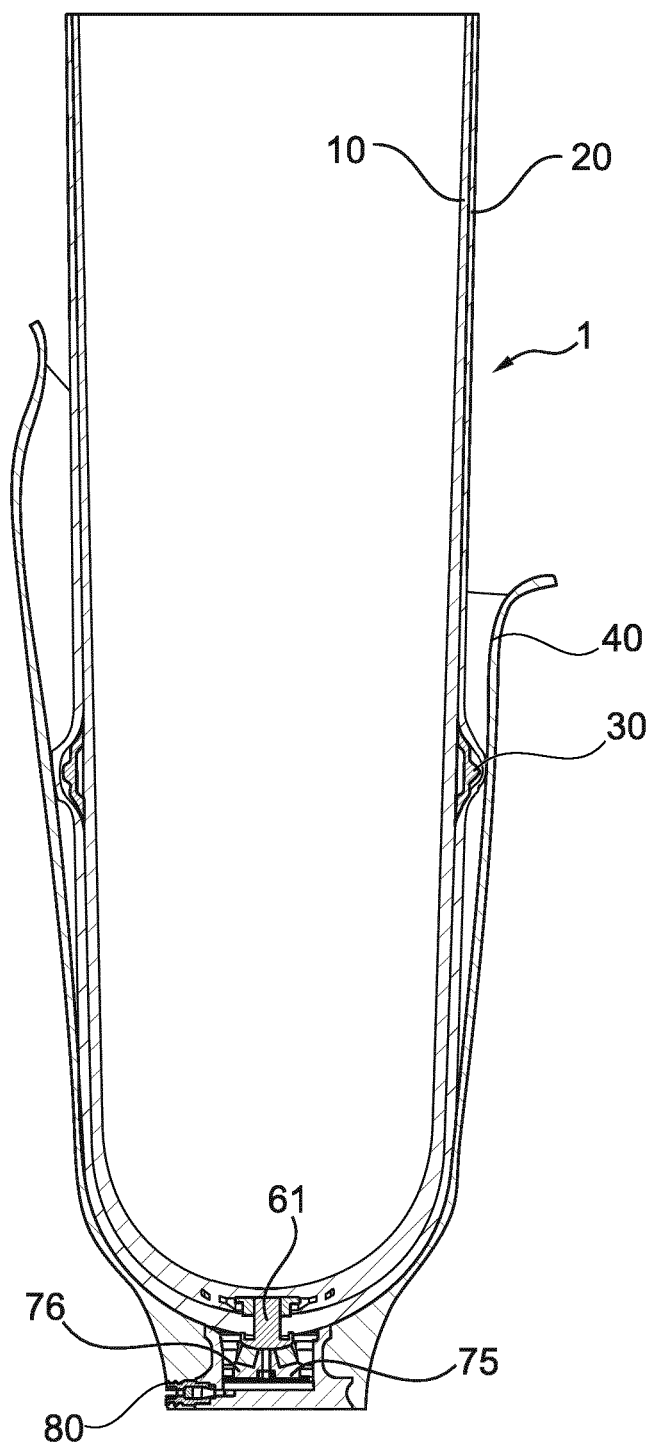

FIGS. 19 to 21 schematically depict another variation of the invention. The basic structure of the prosthetic liner system 1 corresponds to the structure in FIG. 18; however, a bracket 60 is integrated into the inner liner 10, wherein said bracket is situated in the distal end region 11 of the inner liner 10. The bracket 60 is preferably arranged centrally in the inner liner 10; in particular, it is laminated or moulded in said inner liner. The bracket 60 can extend up to the outer wall 16 of the inner liner 10. A pin 61 is arranged inside of the bracket; for example, said pin is inserted, screwed in or pressed in. The pin 61 protrudes through the outer liner 20 and has a distal head 62, which lies flat on the outer side 26 of the outer liner 20. The head 62 may be arranged on the pin 61 as a separate component. The head 62 may be made of a ferromagnetic material, it may comprise a ferromagnetic coating or be equipped with magnets, or be designed as a magnet.

If the liner system 1 is inserted into the prosthetic socket 40, as shown in FIG. 19, the outer circumference abuts the inner wall 41 of the prosthetic socket 40 in the vicinity of the sealing element 30. Graphically, this is depicted by the original outer contour of the liner system 1 protruding beyond the inner contour of the prosthetic socket 40. During actual use, the sealing lip 30, and therefore also the outer liner 20, would deform and adjust to the inner contour on the inner surface 41 of the prosthetic socket 40, and seal a closed volume between the inner wall 41 of the prosthetic socket 40 and the outer liner 20.

A thickening or projection is designed inside the prosthetic liner 40 in the distal end region 42, an insert 70 being incorporated or fixed in said thickening or projection, wherein further prosthetic components can be fixed to said insert in the distal direction. A recess 74 is provided in the insert 70, in which a piston 75 is mounted such that it can be displaced in the distal-proximal direction. The recess 74 is preferably designed to be cylindrical. In the example of an embodiment shown, several magnets 76 are arranged in the correspondingly formed piston 75 in order to guarantee a force-locking coupling to the prosthetic liner system 1 via the head 62. Together with the insert, the piston 75 and the recess 74 form a pump chamber, which is fluidically connected to an outlet valve 80. A flow passage 78 equipped with a valve 77 may be provided inside the piston 75 in order to suck air out of the volume between the prosthetic socket 40 and the liner system 1 during a movement of the pump and to transport it through the outlet valve 80 into the surrounding environment.

FIG. 20 shows the configuration according to FIG. 19 when mounted, wherein the pin 61 is in contact, via the head 62, with the piston 75 and the magnets 76 arranged on it. A force-locking connection between the piston 75 and the prosthetic liner system 1 is created via the magnets 76 and the—where appropriate magnetic, at least ferromagnetic—head 62. The prosthetic liner system 1 is inserted further into the prosthetic socket 40 in the distal direction, the seal 30 runs along the inner side 41 of the prosthetic socket 40 and, due to the gradual convergence of the inner wall 41, is not more dramatically deformed to fit the outer contour of the outer liner 20, which is not expanded by the sealing element 30. Graphically, this is depicted by the increased coverage of the components, shown to be undeformed, formed of the prosthetic socket 40 and the prosthetic liner system 1. The closed volume 90 is also shown, which forms between the sealing arrangement of the sealing element 30 and the outer liner 20 to the inner wall 41 of the prosthetic socket in the proximal area and the closed configuration of the prosthetic socket 40 in the distal area. The pump volume, which is at a maximum in the situation depicted as the piston 75 is in the proximal position, is reduced by the further insertion of the prosthetic liner system 1 in the distal direction, until the outer liner 20 lies fully on the distal inner end of the prosthetic socket 40. This situation is depicted in FIG. 21. The volume enclosed in the recess 74 in the pump volume is pushed out through the outlet valve 80. Such a pumping motion occurs, for instance, during the stance phase when walking or while standing. If the prosthetic socket 40 is relieved of a load, i.e. moved in the distal direction relative to the prosthetic liner system 1, for example during a swing phase or a relief phase, the force-locking connection between the pin 61 and the piston 75 causes the piston 75 to be displaced in the proximal direction. Air can be sucked out of the closed volume 90 via the valve 77, wherein said air may have gotten in via a leak, and released through the outlet valve 80 during the next load. The valves 77, 80 may also be designed as switch valves so as to enable an aeration of the volume 90 when stepping out of the prosthetic socket.

Alongside a depicted magnetic coupling between the piston 75 and the prosthetic liner system 1, said coupling may also be conducted in another, force-locking, manner; in principle, positive-locking couplings are also included, for example via an elastic snap lock, velcro fasteners, a bayonet mechanism or similar.

An active pump can be connected to the outlet valve 80 to create negative pressure in the pump volume formed by the piston 75 and the recess 74, thereby guaranteeing an additional securing of the prosthetic liner 1 inside of the prosthetic socket 40.

We claim:

1. A liner system for applying to a limb or a limb stump, the liner system comprising:
   a socket comprising an inner wall;
   an inner liner comprising an inner side facing the limb or limb stump and an outer side facing away from the limb or limb stump;
   an outer liner that comprises an inner side facing the inner liner and an outer side facing the inner wall of the socket and facing away from the inner liner and that is applied over the inner liner;
   a sealing element separate from the inner liner and the outer liner and comprising two free ends and at least one fixing element for attaching the free ends to one another, the sealing member being between the outer side of the inner liner and the inner side of the outer liner, wherein the sealing element is ring-shaped, wherein the sealing element is configured to be held in place on the outer side of the inner liner by an elastic holding force and is displaceable along a longitudinal direction of the inner liner before the outer liner is applied to the inner liner and the sealing element, and wherein the sealing element is configured to be held in place between the outer side of the inner liner and the inner side of the outer liner by pressure exerted on the sealing element and the inner liner by the outer liner.

2. The liner system according to claim 1, wherein the fixing element is configured on or fixed to the sealing element.

3. The liner system according to claim 1, wherein a cross-section of the sealing element is solid or has a closed or open hollow cross-section.

4. The liner system according to claim 3, wherein the sealing element comprises a foam material or features or is filled with a foam material or a textile.

5. The liner system according to claim 1, wherein a cross-section of the sealing element is round, triangular, quadrangular or polygonal, or with a flat contact surface.

6. The liner system according to claim 1, wherein the sealing element is elastic or is made of an elastic material.

7. The liner system according to claim 1, wherein the sealing element sticks to the outer side of the inner liner and/or to the inner side of the outer liner.

8. The liner system according to claim 1, wherein at least one of the inner liner and the outer liner comprise a closed distal end region.

9. The liner system according to claim 1, wherein the inner liner and the outer liner are attached to one another.

10. The liner system according to claim 9, wherein the inner liner and the outer liner are connected to one another in their distal end regions in either a positive-locking or bonded manner, and form a connection zone.

11. The liner system according to claim 10, wherein the connection zone does not extend beyond up to a first distal third of the outer liner in a proximal direction.

12. The liner system according to claim 1, wherein at least one of the inner liner and the outer liner comprises a closed cross-section.

13. The liner system according to claim 1, wherein the outer liner or the inner liner and the outer liner are elastic or made of an elastomer.

14. The liner system according to claim 1, wherein the inner liner and the outer liner are made of the same material.

15. The liner system according to claim 1, further comprising markers arranged on the inner liner to align the sealing element.

16. The liner system according to claim 1, wherein the inner liner forms a smooth-walled inner surface along with the outer liner.

17. The liner system according to claim 1, wherein the outer liner is designed such that it can be shortened.

18. A method for applying a liner system according to claim 1, the method comprising the steps of:
   Providing the liner system of claim 1,
   applying the inner liner around the limb or the limb stump, followed by applying the sealing element on the outer side of the inner liner, followed by applying the outer liner on the outer side of the inner liner and covering of the sealing element with the outer liner.

19. The method according to claim 18, wherein, upon or following the application of the inner liner, the outer liner is arranged at least partially over the outer side of the inner liner; a proximal end of the outer liner is subsequently pulled down in the distal direction before the application of the sealing element; and the pulled-down distal end of the outer liner is subsequently moved over the sealing element applied on the inner liner.

20. The method according to claim 18, wherein the sealing element is applied on the outer side of the inner liner transversely or perpendicular to a longitudinal direction of the inner liner.

21. The method according to claim 18, wherein the sealing element is fixed to the inner liner following or upon the application to the outer side of the inner liner.

22. A liner system for applying to a limb or a limb stump, the liner system comprising:
  an inner liner comprising an inner side facing the limb or limb stump;
  an outer side facing away from the limb or limb stump;
  an outer liner that comprises an inner side facing the inner liner and an outer side facing away from the inner liner and that is applied over the inner liner;
  a sealing element separate from the inner liner and the outer liner, the sealing element being between the outer side of the inner liner and the inner side of the outer liner, wherein the sealing element includes two free ends and at least one fixing element for attaching the free ends to one another, wherein the sealing element is configured to be held in place on the outer side of the inner liner by an elastic holding force and is displaceable along a longitudinal direction of the inner liner before the outer liner is applied to the inner liner and the sealing element, and wherein the sealing element is configured to be held in place between the outer side of the inner liner and the inner side of the outer liner by pressure exerted on the sealing element and the inner liner by the outer liner.

* * * * *